US006825166B2

(12) United States Patent
McChesney et al.

(10) Patent No.: US 6,825,166 B2
(45) Date of Patent: Nov. 30, 2004

(54) MOLECULAR CONJUGATES FOR USE IN TREATMENT OF CANCER

(75) Inventors: James D. McChesney, Boulder, CO (US); Madhavi C. Chander, Boulder, CO (US); Teruna J. Siahaan, Lawrence, KS (US); Christine R. Xu, Tustin, CA (US); Sterling K. Ainsworth, Lyons, CO (US)

(73) Assignee: Tapestry Pharmaceuticals, Inc., Boulder, CO (US)

( * ) Notice: Subject to any disclaimer, the term of this patent is extended or adjusted under 35 U.S.C. 154(b) by 0 days.

(21) Appl. No.: 10/107,543

(22) Filed: Mar. 25, 2002

(65) Prior Publication Data
US 2002/0198141 A1 Dec. 26, 2002

Related U.S. Application Data
(60) Provisional application No. 60/278,243, filed on Mar. 23, 2001.

(51) Int. Cl.[7] .................. A61K 31/337; A61K 31/436; A61K 38/40; C07D 311/88; C07K 1/113
(52) U.S. Cl. .............. 514/2; 424/9.6; 514/6; 514/8; 514/34; 514/182; 514/283; 514/449; 514/454; 530/345; 530/395; 530/409; 530/410; 536/6.4; 546/48; 549/227; 549/510; 552/544
(58) Field of Search .............. 424/9.6; 514/2, 514/6, 8, 12, 21, 34, 182, 283, 449, 454; 530/345, 395, 408, 409, 410; 536/4.1, 6.4, 16.8, 17.2, 18.1; 546/48; 549/227, 510; 552/544

(56) References Cited
U.S. PATENT DOCUMENTS
4,522,750 A 6/1985 Ades et al. ............. 530/397
4,625,014 A 11/1986 Senter et al. ........... 530/300

(List continued on next page.)

FOREIGN PATENT DOCUMENTS
| EP | 0 624 377 A2 | 11/1994 |
| EP | 1 033 372 A1 | 9/2000 |
| WO | WO 97/44026 | 11/1997 |
| WO | WO 98/19705 | 5/1998 |
| WO | WO 98/52614 | 11/1998 |

OTHER PUBLICATIONS

Yeh et al., "Killing of Human Tumor Cells in Cülture with Adriamycin Conjugates of Human Transferrin", Clin. Immunol. Immunopathol. 32, 1–11 (1984).

(List continued on next page.)

Primary Examiner—Jeffrey Edwin Russel
(74) Attorney, Agent, or Firm—Timothy J. Martin; Michael R. Henson; Rebecca A. Gegick

(57) ABSTRACT

A molecular conjugate is provided having the formula:

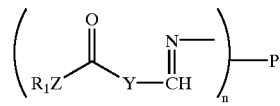

wherein n is the conjugation number, P is a moiety of a carrier molecule such as a protein, $R_1$ is a moiety of a biologically active molecule or its analogs, derivatives, salts or secondary amines, Z is —O— or —NH—, and Y is a straight or branched alkyl having 1 to 20 carbons optionally substituted with one or more phenyl, a cycloalkyl optionally substituted with one or more alkyl or phenyl, or an aromatic group optionally substituted with one or more alkyl, electron-withdrawing or electron-donating groups. Compounds and methods useful in producing such molecular conjugates are also provided, as well as methods of concentrating biologically active molecules in selected target cells of a patient that comprise administering to the patient a selected dose of such molecular conjugates.

68 Claims, 21 Drawing Sheets

U.S. PATENT DOCUMENTS

| | | | |
|---|---|---|---|
| 4,631,190 A | 12/1986 | Shen et al. | 424/181.1 |
| 4,886,780 A | 12/1989 | Faulk | 514/8 |
| 5,108,987 A | 4/1992 | Faulk | 514/8 |
| 5,144,011 A | 9/1992 | Shen et al. | 530/391.5 |
| 5,254,342 A | 10/1993 | Shen et al. | 424/401 |
| 5,354,844 A | 10/1994 | Beug et al. | 530/345 |
| 5,387,578 A | 2/1995 | Angelucci et al. | 514/21 |
| 5,393,737 A | 2/1995 | Mayers et al. | 514/12 |
| 5,501,854 A | 3/1996 | Raso | 424/136.1 |
| 5,527,527 A | 6/1996 | Friden | 424/178.1 |
| 5,571,082 A | 11/1996 | Bashikirov | 604/4 |
| 5,599,908 A | 2/1997 | Raso | 530/387.3 |
| 5,603,931 A | 2/1997 | Raso | 424/136.1 |
| 5,614,487 A | 3/1997 | Battersby et al. | 514/2 |
| 5,672,683 A | 9/1997 | Friden et al. | 530/350 |
| 5,675,025 A | 10/1997 | Sisti et al. | 549/510 |
| 5,684,175 A | 11/1997 | Sisti et al. | 560/27 |
| 5,688,977 A | 11/1997 | Sisti et al. | 549/410 |
| 5,728,383 A | 3/1998 | Johnson et al. | 424/183.1 |
| 5,750,737 A | 5/1998 | Sisti et al. | 549/510 |
| 5,762,932 A | 6/1998 | Kemp | 424/143.1 |
| 5,770,745 A | 6/1998 | Swindell et al. | 549/510 |
| 5,795,560 A | 8/1998 | Reed | 424/9.1 |
| 5,808,113 A | 9/1998 | Murray et al. | 549/510 |
| 5,833,988 A | 11/1998 | Friden | 424/178.1 |
| 5,939,566 A | 8/1999 | Swindell et al. | 549/510 |
| 5,948,919 A | 9/1999 | Sisti et al. | 549/510 |
| 5,973,170 A | 10/1999 | Sisti et al. | 549/510 |
| 5,977,307 A | 11/1999 | Friden et al. | 530/350 |
| 6,015,555 A | 1/2000 | Friden | 424/133.1 |
| 6,027,921 A | 2/2000 | Heartlein et al. | 435/69.7 |
| 6,048,990 A | 4/2000 | Liang et al. | 549/510 |
| 6,066,749 A | 5/2000 | Sisti et al. | 549/510 |
| 6,072,060 A | 6/2000 | Swindell et al. | 549/510 |
| 6,077,834 A | 6/2000 | Cheng | 514/44 |
| 6,107,497 A | 8/2000 | Sisti et al. | 549/510 |
| 6,133,462 A | 10/2000 | Sisti et al. | 549/510 |
| 6,136,999 A | 10/2000 | Chander et al. | 560/21 |
| 6,143,902 A | 11/2000 | Zygmunt et al. | 548/435 |
| 6,150,327 A | 11/2000 | Sinn et al. | 514/8 |
| 6,171,612 B1 | 1/2001 | Byk et al. | 424/450 |
| 6,191,290 B1 | 2/2001 | Safavy | 549/510 |
| 6,262,281 B1 | 7/2001 | Swindell et al. | 549/510 |
| 6,307,088 B1 | 10/2001 | Swindell et al. | 560/27 |
| 2001/0000488 A1 | 4/2001 | Mather | 435/69.1 |

OTHER PUBLICATIONS

Sizensky et al., "Characterization of the Anti–Cancer Activity of Transferrin–Adriamycin Conjugates", Am.J. Reprod. Immunol. 27:163–166 (1992).

Kratz et al., "Transferrin Conjugates of Docurubicin: Synthesis, Characterization, Cellular Uptake, and in Vitro Efficacy", J. Pharm Sci., 87, 338–346 (1998).

Tanaka et al., "Synthesis of Transferrin–Mitomycin C Conjugate as a Receptor–Mediated Drug Targeting System", Biol. Pharm. Bull. 19, 774–777 (1996).

Bicamumpaka et al., "In Vitro Cytotoxicity of Paclitaxel–Transferrin Conjugate on H69 Cells", Oncol. Rep., 5, 1381–1383 (1998).

Skehan et al., "New Colorimetric Cytotoxicity Assay for Anticancer–Drug Screening", J. Natl. Cancer Inst. 82: 1107–1112, (1990).

Likhitwitayawuid et al., "Cytotoxic and Antimalarial Bis-benzylisoquinoline Alkaloids from Stephania Erecta." J. Nat. Prod. 56: 30–38, (1993).

Ojima et al. "Macrocycle Formation by Ring–Closing Metathesis Application to the Syntheses of Novel Macrocyclic Taxoids" Journal of the American Chemical Society, 2000, vol. 122, pp. 5343–5353.

Singh et al. "Transferrin Directed Delivery of Adriamycin to Human Cells", Anticancer Research, 1998, vol. 18, pp. 1423–1428.

MOLECULAR CONJUGATES FOR USE IN TREATMENT OF CANCER

CROSS-REFERENCE TO RELATED APPLICATIONS

This application claims the benefit of U.S. Provisional Application No. 60/278,243, filed Mar. 23, 2001.

FIELD OF THE INVENTION

The present invention generally relates to chemical compounds and methods for use in treating patients. More particularly, the present invention is directed to molecular conjugates for use in cancer treatment. Specifically, the present invention relates to Transferrin-drug conjugates, methods and intermediates useful in the formation thereof, and methods for treating a patient therewith.

BACKGROUND OF THE INVENTION

A number of anti-cancer drugs are currently in clinical use for the treatment of various cancers. For example, paclitaxel and taxotere are two promising anti-cancer drugs used to treat breast and ovarian cancers, and which hold promise for the treatment of other cancers such as skin, lung, head and neck carcinomas. Other promising chemotherapeutic agents are being developed or tested for treatment of these and other cancers. Compounds such as paclitaxel, taxotere, and other taxanes, camptothecins, epothilones and quassinoids, as well as other compounds exhibiting efficacy in cancer treatment, are of considerable interest. Of special interest are natural product drugs with demonstrated anticancer activity, in vitro and in vivo. Such compounds are desirable, for example, for their potential availability from renewable resources.

However, many identified anti-cancer compounds present a number of difficulties with their use in chemotherapeutic regimens. One particular problem relates to the aqueous insolubility of many anti-cancer compounds, which creates significant problems in developing suitable pharmaceutical formulations useful for chemotherapy. In an attempt to increase the aqueous solubility of these drugs, they are often formulated with various carrier compounds. However, these carrier compounds often cause various adverse side effects in a patient treated with the formulation. For example, paclitaxel and camptothecin and their analogs are generally formulated with a mixture of polyethoxylated castor oil (Cremophore) and ethanol. This mixture has been reported to cause side effects in clinical trials, which include neutropenia, mucositis, cardiac and neurological toxicities, hypersensitivity, histamine release and severe allergic reactions.

Another problem with the use of such chemotherapeutic agents in cancer treatment is the difficulty targeting cancer cells without adversely affecting normal, healthy cells. For example, paclitaxel exerts its antitumor activity by interrupting mitosis and the cell division process, which occurs more frequently in cancer cells than in normal cells. Nonetheless, a patient undergoing chemotherapy treatment may experience various adverse side effects associated with the interruption of mitosis in normal, healthy cells.

Accordingly, it would be highly desirable to develop chemical compounds and methods for use in directly targeting cancer cells with chemotherapeutic agents in cancer treatment regimens. This, in turn, could lead to reduction or elimination of toxic side effects from carrier compounds, more efficient delivery of the drug to the targeted site, and reduction in dosage of the administered drug and a resulting decrease in toxicity to healthy cells and in the cost of administering the chemotherapeutic regimen.

One particular approach of interest is the use of anti-cancer drug moieties that have been conjugated to tumor-recognizing molecules. For example, U.S. Pat. No. 6,191,290 to Safavy discusses the formation and use of a taxane moiety conjugated to a receptor ligand peptide capable of binding to tumor cell surface receptors. Safavy in particular indicates that such receptor ligand peptides might be BBN/GRP receptor-recognizing peptide, a somatostatin receptor-recognizing peptide, an epidermal growth factor receptor-recognizing peptide, a monoclonal antibody or a receptor-recognizing carbohydrate.

One tumor-recognizing molecule of particular interest is the human protein Transferrin. Transferrin is a serum glycoprotein of approximately 79550 molecular weight, which is involved in iron transport to developing red cells for hemoglobin synthesis. It has a very high binding affinity for ferric iron so that essentially no free ferric iron, a very toxic form of iron, occurs in plasma. Further, the iron requirement of growing cells is provided by diferric Transferrin (each protein molecule specifically binds with two $Fe^{3+}$ ions to form salmon-pink complexes) which binds to receptors on the cell membrane leading to an internalization of the Transferrin-receptor complex which then leads to a release of iron to the cytoplasm of the cell and return of the apoTransferrin-receptor complex to the cell surface and release of the apoTransferrin from the receptor. It has been demonstrated that growing cells have Transferrin receptors on their cell surface whereas static cells either do not or have very low numbers of Transferrin receptors. Further, cancer cells have been demonstrated to have a high number of Transferrin receptors and interestingly, drug resistant cancer cells have an even greater number of Transferrin receptors. The presence of Transferrin receptors on cancer cells but not on normal cells suggests that Transferrin conjugates could provide a selective way of targeting agents to cancer cells. For instance, as reported by Yeh et al., "Killing of Human Tumor Cells in Culture with Adriamycin Conjugates of Human Transferrin", *Clin. Immunol. Immunopathol.* 32, 1–11 (1984), and by Sizensky et al., "Characterization of the Anti-Cancer Activity of Transferrin-Adriamycin Conjugates", *Am. J. Reprod. Immunol.* 27:163–166 (1992), Transferrin-adriamycin conjugates have a higher therapeutic index than free adriamycin for cancer therapy.

Other works suggest a promising approach to cancer therapies utilizing Transferrin conjugated with various chemotherapeutic drugs, such as Doxorubicin (Kratz et al., "Transferrin conjugates of Docorubicin: Synthesis, Characterization, Cellular Uptake, and in Vitro Efficacy", *J. Pharm Sci.*, 87, 338–346 (1998)) and Mytomycin C (Tanaka et al., "Synthesis of Transferrin-Mitomycin C Conjugate as a Receptor-Mediated Drug Targeting System", *Biol. Pharm. Bull.* 19, 774–777 (1996)).

An attempt at an effective Transferrin-paclitaxel conjugate was reported by Bicamumpaka et al., "In Vitro Cytotoxicity of Paclitaxel-Transferrin Conjugate on H69 Cells", *Oncol. Rep.*, 5, 1381–1383 (1998). In particular, Bicamumpaka et al. synthesized 2'-glutaryl-hexanediamine paclitaxel, which was then coupled to Transferrin using a glutaraldehyde linker through an amino of the 2'-glutaryl-hexanediamine group. However, Bicamumpaka reported that the capacity of the resulting Transferrin-paclitaxel conjugate to inhibit growth of H69 cells was 5.4 times less than that of the native paclitaxel drug.

Accordingly, it can be seen that there is a need to provide new chemical compounds for linking chemotherapeutic agents to various molecules, such as Transferrin, the receptor ligand peptides recognized by Safavy, or other proteins, antibodies, lectins or other substances that may become attached to the surface of a cell. There is also a need to provide methods for forming such compounds. It can further be seen that there is a need for new molecular conjugates for use in treating cancer, and Transferrin-drug conjugates in particular. Finally, there is a need for new methods of administering chemotherapeutic pharmaceutical formulations to patients for use in cancer treatment regimens, such as through the use of improved molecular conjugates such as Transferrin-drug conjugates. The present invention is directed to meeting these needs.

SUMMARY OF THE INVENTION

It is an object of the present invention to provide new and useful compositions of molecular conjugates of hydroxyl-bearing or amino-bearing drugs.

It is a further object to provide compositions of Transferrin-drug conjugates for use in treating cancer.

It is another object to provide intermediate compounds for use in forming molecular conjugates, such as Transferrin-drug conjugates, for use in treating cancer.

It is yet another object to provide efficient methods for the formation of molecular conjugates, and Transferrin-drug conjugates in particular.

A still further object is to provide new and useful methods for administering chemotherapeutic agents to patients that reduce or eliminate side effects conventionally experienced by cancer patients.

A still further object of the present invention is to provide methods for efficiently concentrating chemotherapeutic agents in cancer cells of a patient.

According to the present invention, then, a molecular conjugate is provided having the formula:

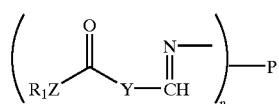

wherein n is a conjugation number of the molecular conjugate, such as an integer from 1 to 5, P is a de-amino moiety of a molecule having at least n accessible amino functionalities, such as a Transferrin protein, $R_1$ is a de-hydroxyl or de-amino moiety respectively of a hydroxyl-bearing or amino-bearing biologically active molecule or an analog or derivative thereof, and Z is —O— or —NH—, respectively, Y is a straight or branched alkyl having 1 to 20 carbons that may be optionally substituted with one or more phenyl, a cycloalkyl optionally substituted with one or more alkyl or phenyl, or an aromatic group optionally substituted with one or more alkyl groups, electron-withdrawing groups, or electron-donating groups. P is preferably a protein, such as Transferrin, that is conjugated through the linkage structure with the biologically active molecule, which may be a natural product drug, such as one useful in cancer therapy, and may include various taxanes, camptothecins, epothilones, cucurbitacins, quassinoids, anthracyclines, and their analogs and derivatives.

The present invention also relates to compounds useful in the formation of molecular conjugates, such as Transferrin-drug conjugates. The compounds have the generalized formula:

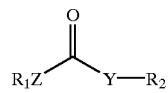

wherein $R_1$, Y and Z are as above and $R_2$ is —CH=CH(W), —CH(OH)CH(OH)W, or —C(O)H, where W can be H, a straight or branched alkyl having 1 to 20 carbons that may be optionally substituted with one or more phenyl, a cycloalkyl optionally substituted with one or more alkyl or phenyl, or an aromatic group optionally substituted with one or more alkyl groups, electron-withdrawing groups, or electron-donating groups.

The present invention additionally relates to methods of producing molecular conjugates according to the present invention, and in particular Transferrin-drug conjugates for use in the treatment of cancer. The method comprises the steps of reacting a first compound of either a hydroxyl-bearing or amino-bearing biologically active molecule and analogs and derivatives (and salts or secondary amines) thereof with a second compound of either formula

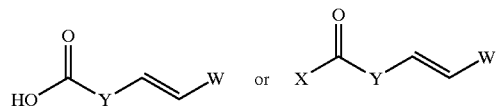

thereby to form a third compound of the formula:

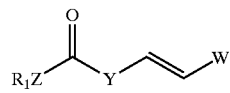

converting the third compound to a fourth compound of the formula:

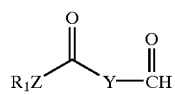

and conjugating the fourth compound with a molecule having at least n accessible amino functionalities, thereby to form a molecular conjugate of the formula:

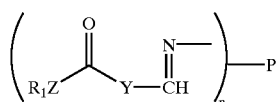

where X is a halogen and $R_1$, Z, W, Y, n and P are as above. W is preferably H such that the second compound has a terminal olefin. The step of converting the third compound to the fourth compound may go through the intermediate formation of a corresponding diol of the formula:

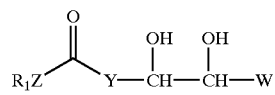

by oxidizing the third compound to the diol and thereafter oxidizing the diol to the fourth compound.

The present invention further provides methods of producing Transferrin-7-paclitaxel conjugates, Transferrin-2'- paclitaxel conjugates, Transferrin-3'-paclitaxel conjugates and Transferrin-20-camptothecin conjugates. The present invention also provides Transferrin-rhodamine123 compounds, as well as intermediates and methods for use in the production thereof.

Finally, the present invention relates to methods of concentrating biologically active molecules in selected target cells of a patient utilizing the conjugate compounds of the present invention, In particular, the method comprises administering to the patient a selected dose of a molecular conjugate according to the present invention, such as a Transferrin-drug conjugate.

These and other objects of the present invention will become more readily appreciated and understood from a consideration of the following detailed description of the exemplary embodiments of the present invention when taken together with the accompanying drawings, in which:

DETAILED DESCRIPTION OF THE EXEMPLARY EMBODIMENTS

Figure 1:
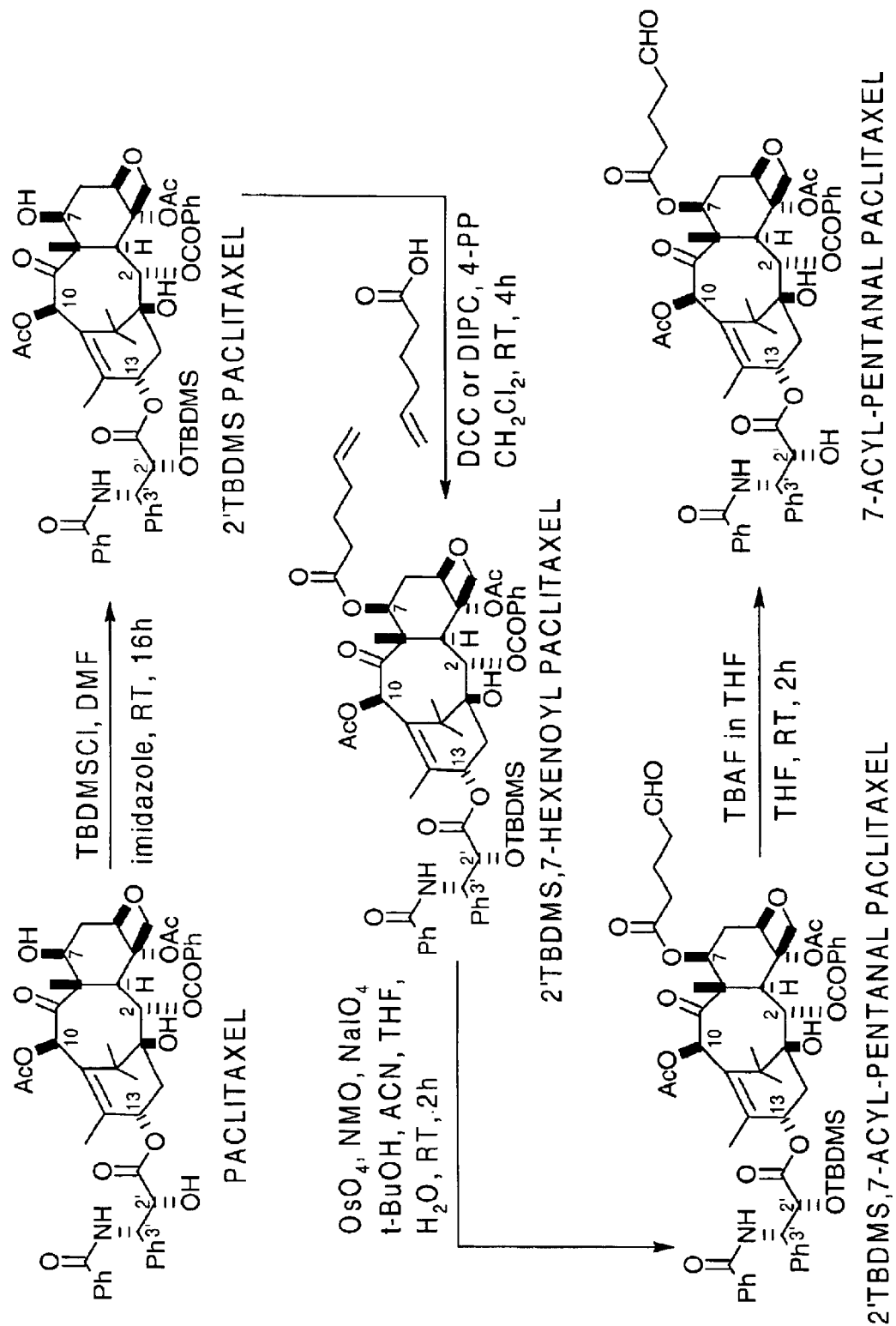
FIG. 1 shows a chemical reaction scheme for forming a 7-acyl-pentanal paclitaxel linker compound for use in forming a Transferrin-7-paclitaxel conjugate.

The present invention provides new molecular conjugates, and in particular new Transferrin-drug conjugates for use in treating cancer in a patient. Additionally, the present invention is directed to novel intermediate compounds for use in linking biologically active molecules to carrier molecules such as Transferrin or other molecules. In particular, the present invention provides aldehyde ester and amido derivatives, respectively, of hydroxyl-bearing and amine-bearing biologically active molecules, such as cancer therapeutic drugs and analogs and derivatives thereof, as well as precursors thereto, which can be linked to carrier molecules such as human Transferrin protein through the formation of Schiff bases between the aldehyde functionality of the ester or amide linkage and various amino functionalities of the Transferrin molecule or other protein.

The present invention also provides an efficient protocol for the synthesis of Transferrin conjugates, or other molecular conjugates, of various hydroxyl-bearing or amino-bearing biologically active compounds, and intermediates thereto. A generalized process includes coupling such hydroxyl-bearing or amino-bearing biomolecules with an appropriate acylating agent, such as a carboxylic acid or acid halide, having a double bond, preferably a terminal olefin. A rapid and highly efficient oxidation of the terminal olefin site using catalytic osmium tetroxide followed by cleavage of the resulting diol to aldehyde provides a suitable precursor for synthesis of Transferrin conjugates or other molecular conjugates. The final step in the synthetic sequence of these adducts is the treatment of the aldehyde with a carrier molecule such as the blood protein Transferrin to make biomolecules attached to monomeric Transferrin, which are found to have an increased biological activity. In place of Transferrin, the present invention broadly contemplates that carrier molecules may include any molecule having at least one accessible amino functionality through which a Schiff base may be formed with the aldehyde functionality of the ester and amido linker compounds of biologically active molecules, as disclosed herein.

It should also be appreciated that the present invention broadly construes the term "biologically active molecule" as including any molecule that generally affects or is involved in or with one or more biological processes in cells, tissues, vessels, or the like. Such biologically active molecules may comprise drugs, antibodies, antigens, lectins, dyes, stains, tracers or any other such molecule. In particular, hydroxyl-bearing or amino-bearing molecules contemplated for use in the invention include paclitaxel, docetaxel and other taxanes, cholesterol, rhodamine 123, camptothecins, epothilones such as epothilone B, cucurbitacins, quassinoids such as glaucarubolone, brusatol and bruceantin, anthracyclines such as adriamycin, daunorubicin and the like, and their analogs and derivatives, as well as other compounds. The term "molecular conjugate" should be understood to broadly encompass any compound comprising a biologically active molecule linked to a carrier molecule according to the present invention, such as through the ester and amide Schiff base linkages disclosed herein.

It should further be understood that, while the focus of this work is directed to cancer therapy, the present application contemplates the conjugation according to the present invention of various proteins or other carrier molecules with biologically active molecules directed toward other applications.

I. Transferrin-7-Paclitaxel Conjugate

A Transferrin-7-paclitaxel conjugate can be formed according to the present invention. As shown in FIG. 1, paclitaxel is first converted to a 7-paclitaxel aldehyde ester through various intermediate compounds. The aldehyde ester is then linked to Transferrin to form a Transferrin-7-paclitaxel conjugate.

A. Preparation of 2'TBDMS Paclitaxel

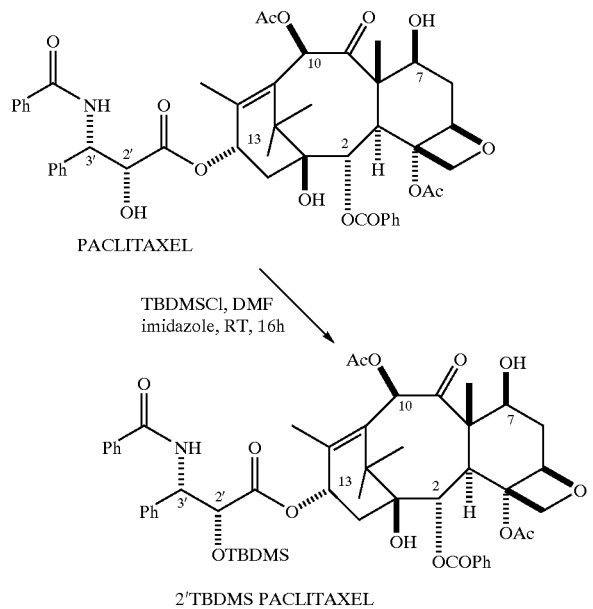

Paclitaxel was first protected at the 2'-hydroxyl with TBDMS to form 2'-TBDMS paclitaxel. While TBDMS is shown in the exemplary reaction, it should be appreciated that other protecting groups, such as TROC, BOM, CBZ, benzyl, TES, EE or the like, may be used in place of TBDMS.

This material was prepared according to the procedures described by Prof Gunda Georg et al in Tetrahedron Letters, vol 35, p 8931–8934, 1994 and characterized accordingly.

To a solution of paclitaxel (20.0 g, 23.45 mM) in dimethylformamide (150 mL) was added imidazole (23.95 g, 351.7 mM) under nitrogen atmosphere, followed by the addition of TBDMSCI (49.5 g, 328.3 mM). The resulting solution was stirred at ambient temperatures for 16 h under nitrogen atmosphere. The TLC examination at this stage confirmed complete consumption of the starting material and the reaction was worked up by adding water (200 mL) and ethyl acetate (200 mL). The organic layer was separated and washed with water (2×100 mL), brine (50 mL) and dried over magnesium sulfate, and thereafter filtered and evaporated to a residue, dried in a vacuum oven and used for the following reaction with no further purification.

B. Preparation of 7-hexenoate of 2'protected Paclitaxel

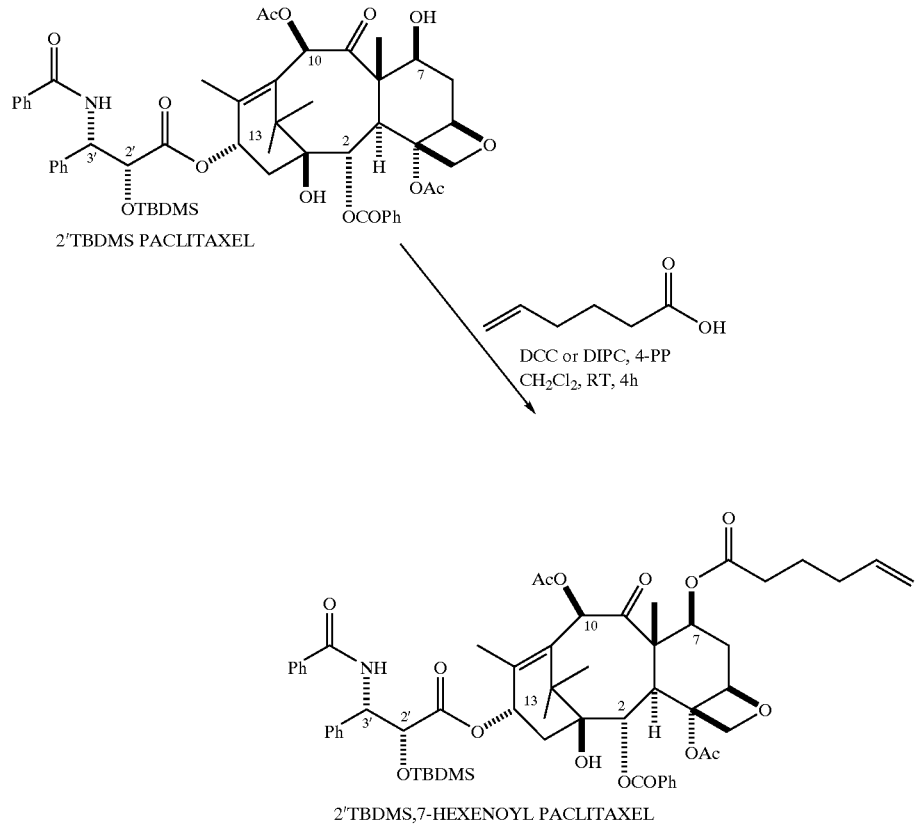

Next, the 7-hexenoate of the 2'-protected paclitaxel was formed by reaction with an acid preferably having terminal olefin. While 5-hexenoic acid is used in the examples herein, it should be appreciated that the present invention contemplates other appropriate acylating agents preferably having terminal olefin, although olefinic acylating agents having the double bond further displaced from the end of the chain are also contemplated. For example, the present invention contemplates the use of acids of the formula:

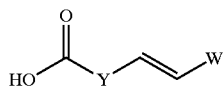

or acid halides of the formula:

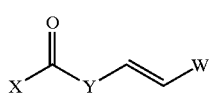

wherein X is a halogen and Y can be a straight or branched alkyl having 1 to 20 carbons optionally substituted with one or more phenyl, a cycloalkyl optionally substituted with one or more alkyl or phenyl, or an aromatic group optionally substituted with one or more alkyl or electron-withdrawing or electron-donating groups. W can be H, a straight or branched alkyl having 1 to 20 carbons optionally substituted with one or more phenyl, a cycloalkyl optionally substituted with one or more alkyl or phenyl, or an aromatic group optionally substituted with one or more alkyl or electron-withdrawing or electron-donating groups.

Here, to a solution of 2'TBDMS paclitaxel (2.0 g, 2.07 mM) in methylene chloride (30 mL) was added 5-hexenoic acid (0.49 mL, 4.14 mM) followed by DIPC (0.81 mL, 5.18 mM) and 4-PP (0.095 g, 0.64 mM) under nitrogen atmosphere. The resulting reaction mixture was stirred for 4 h and deemed complete by TLC analysis. The mixture was worked up by adding water (50 mL) and ethyl acetate (90 mL), and the separated organic layer was washed with water (50 mL), brine (50 mL) and dried over magnesium sulfate. The resulting product was filtered and the solvent evaporated to leave a residue which was subjected to the next reaction with no purification.

C. Preparation of 7-aldehyde Derivative of 2' Protected Paclitaxel

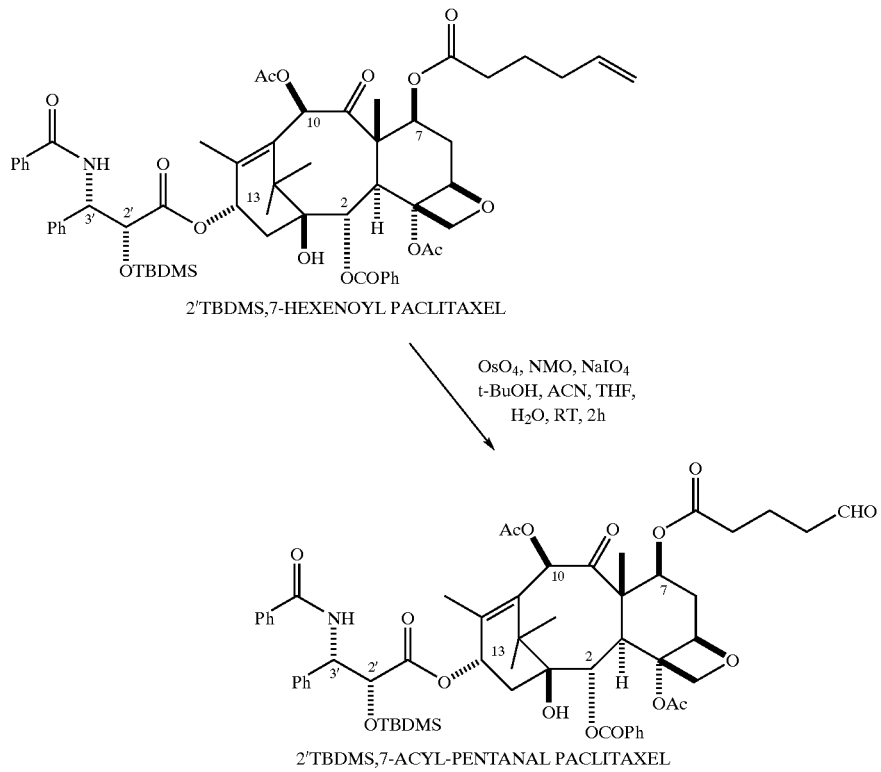

Oxidation of the terminal olefin site to the resulting diol, followed by cleavage of the terminal carbon provides a 7-aldehyde 2'-protected derivative of paclitaxel. Where an acylating agent is used that has the double bond shifted from the end of the chain as discussed above (i.e. where W is not hydrogen in the above formula), it should be appreciated that cleavage of the double bond during this reaction removes the portion of the chain beyond the double bond. Also, while shown as a single step in the exemplary processes, it should be appreciated that the diol of the formula:

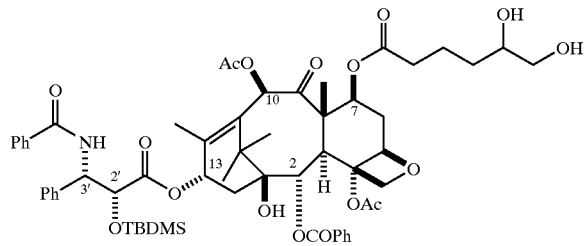

(and corresponding diols of compounds described herein) may be isolated by performing this step in an absence of $NaIO_4$. Oxidative cleavage of the diol on treatment with $NaIO_4$ provides the terminal aldehyde.

To a solution of 7-hexenoyl, 2'TBDMS paclitaxel (2.2 g, 2.07 mM) in ACN and THF (20 mL each) was added water (20 mL) followed by the addition of NMO (0.49 g, 4.14 mM), $NaIO_4$ (0.89 g, 4.14 mM) and $OsO_4$ solution in t-BuOH (13.15 mg, 0.052 mM) under nitrogen atmosphere. The resulting reaction mixture was stirred for 2 h at ambient temperatures and was worked up by adding ethyl acetate and water (100 mL each). The separated organic layer was washed with brine (20 mL) and filtered through magnesium sulfate and sodium hydrosulfite. The filtrate was evaporated to dryness and subjected to desilylation reaction with no purification of the crude product.

D. Preparation of the 7 Aldehyde Derivative of Paclitaxel 1.0 M solution, 3.11 mM) under nitrogen atmosphere at ambient temperatures. The resulting reaction mixture was stirred for 2 h and the TLC examination at this time showed no starting material. The mixture was worked up by adding ethyl acetate (200 mL) and 0.5N HCl (100 mL), and the separated organic layer was washed with water (200 mL), brine (100 mL), and dried over magnesium sulfate. The organic layer was filtered and evaporated to dryness, followed by purification on column chromatography using ethyl acetate and heptane to provide pure material in 60% overall yield. The compound was characterized by MS and $^1H$ NMR.

E. Preparation of Transferrin-7-Paclitaxel Conjugate

The aldehyde ester derivative may next be linked with Transferrin to form a Transferrin-7-paclitaxel conjugate having a conjugation number n (the number of paclitaxel molecules per Transferrin molecule), which was found to be 3, although it is contemplated that varying conditions might produce a Transferrin-7-paclitaxel conjugate having a conjugation number n between 1 and 5. The present invention contemplates, of course, that carrier molecules such as other proteins having accessible amino functionalities may be used in place of Transferrin, and the conjugation number of the resulting molecular conjugate may vary accordingly.

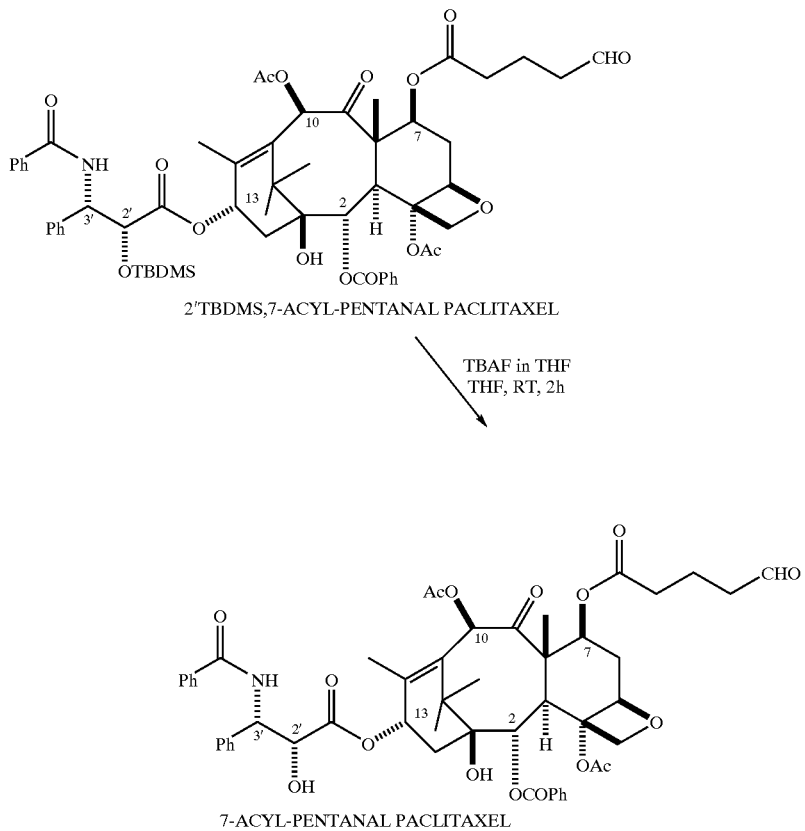

The 2'-position is deprotected as follows. To a solution of 7-aldehyde derivative of 2'protected paclitaxel (2.25 g, 2.07 mM) in THF (50 mL) was added TBAF in THF (3.11 mL of

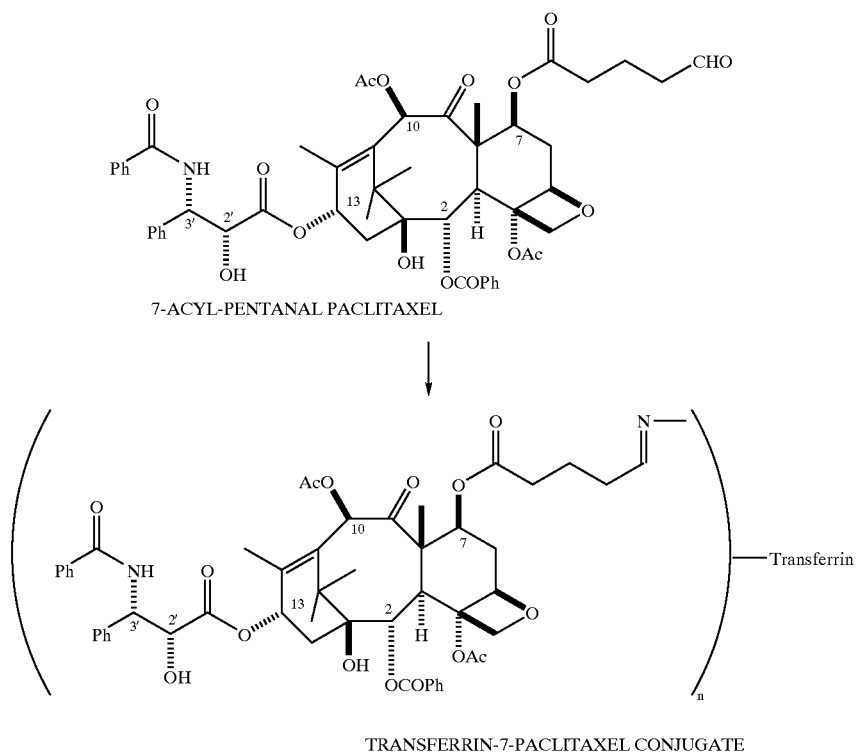

TRANSFERRIN-7-PACLITAXEL CONJUGATE

Here, 2 ml of 19.04 mg (20 μmol) 7-acyl-pentanal paclitaxel in DMSO was added dropwise to 80 mg (1 μmol) Transferrin in PBS-buffer/DMSO solution. Transferrin PBS-buffer/DMSO solution was prepared by dissolving Transferrin in 4 ml PBS (50 mmol pH 8.0), and 2 ml DMSO was added to Transferrin PBS solution at 0° C. The reaction mixture was shaken by C24 incubator shaker (New Brunswick Scientific classic series, Edison, U.S.A.) at 37° C. for 8 h. The reaction mixture was filtered by 5.0 μm filter unit. The clear filtrate was purified using FPLC on a superdex HR200 column (2.0×30 cm) at 0.5 ml/min of 20 mM Tris-HCl (pH 8.0). The fraction corresponding to Transferrin was collected and dried by lyophilization.

While not exemplified herein, it should be appreciated that molecular conjugates of 10-deacetyl paclitaxel are formed similarly to 7-paclitaxel conjugates. For example, a Transferrin-10-acyl-hexanal paclitaxel conjugate is formed similarly to the above-described process using 10-deacetyl paclitaxel of formula:

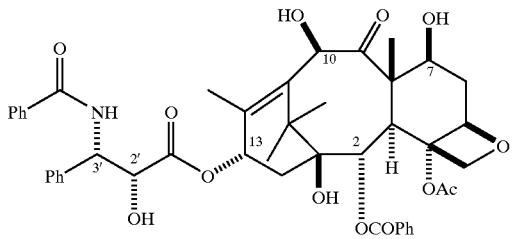

10-DEACETYL PACLITAXEL as a starting compound and using 6-heptenoic acid as an acylating agent. Appropriate protections and deprotections of the 2' and 7 positions may be utilized as known in the art.

II. Transferrin-3-Cholesterol Conjugate

A Transferrin-3-cholesterol conjugate was prepared to investigate the results of linking a non-cytotoxic molecule to Transferrin. As discussed below, these results suggest that the Transferrin-drug conjugates according to the present invention for use in treating cancer should be formed with cancer therapeutic agents having demonstrated in vitro or in vivo cytotoxic activity. Various 3-cholesterol conjugates with other proteins might be similarly prepared for comparison with the conjugation of such proteins with other biologically active compounds, such as for the investigation of applications beyond those of cancer therapeutic molecules, for example.

Figure 2:
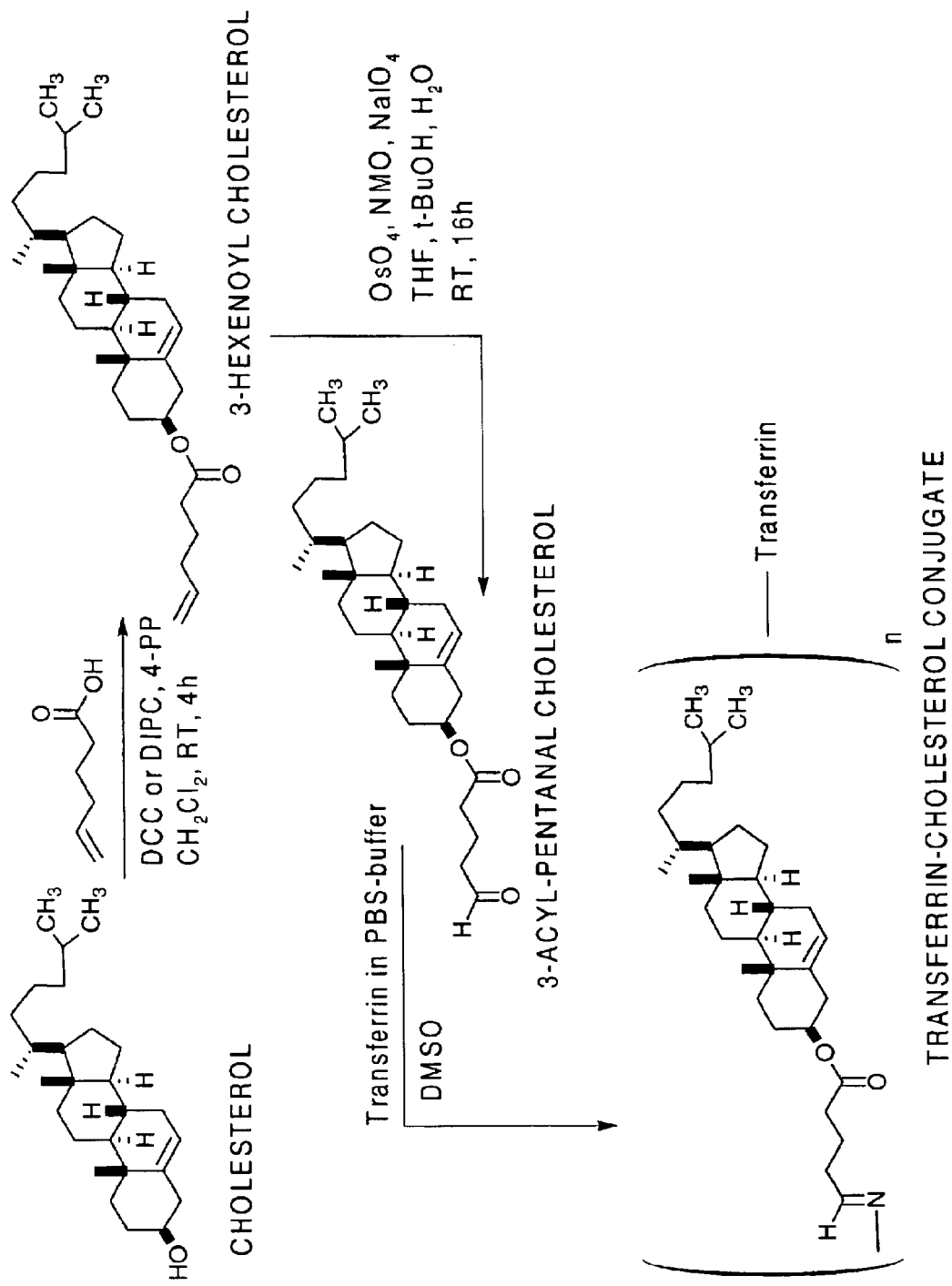
FIG. 2 shows a chemical reaction scheme for forming a Transferrin-3-cholesterol conjugate by linking a 3-acyl-pentanal cholesterol linker compound with Transferrin.

As shown in FIG. 2, cholesterol is first converted through various intermediate compounds to a 3-cholesterol aldehyde ester, which is then linked to Transferrin to form a Transferrin-3-cholesterol conjugate. As previously discussed, various other acylating agents as described above may be substituted for the 5-hexenoic acid used in the examples herein.

A. Preparation of 3-hexenoyl Cholesterol

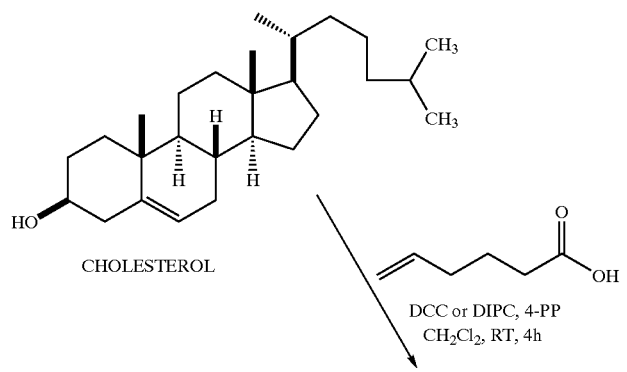

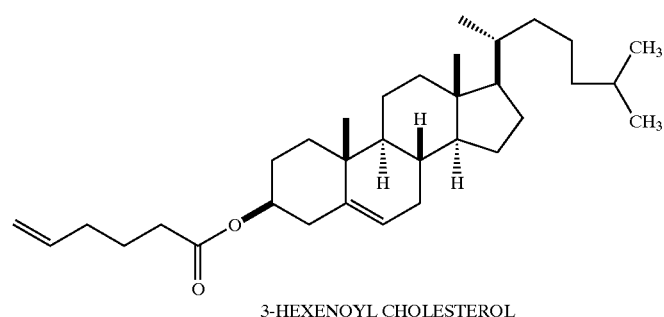

3-HEXENOYL CHOLESTEROL

To a solution of cholesterol (2.0 g, 5.17 mM) in methylene chloride (20 mL) was added 5-hexenoic acid (0.68 mL, 5.69 mM) followed by the addition of DCC (1.60 g, 7.76 mM) and 4-PP (0.115 g, 0.78 mM) under nitrogen atmosphere. The resulting reaction mixture was stirred at ambient temperature for 1 h and worked up with the addition of methyl t-butyl ether (60 mL). The urea was filtered off, and the product was transferred to a separatory funnel, washed with 1N HCl (10 mL), water (30 mL) and brine (30 mL). The product was filtered after drying over MgSO$_4$ and the solvent was evaporated to leave a residue. The product obtained in >95% yield was characterized by $^1$H NMR.

B. Preparation of 3-acyl-pentanal Ester of Cholesterol

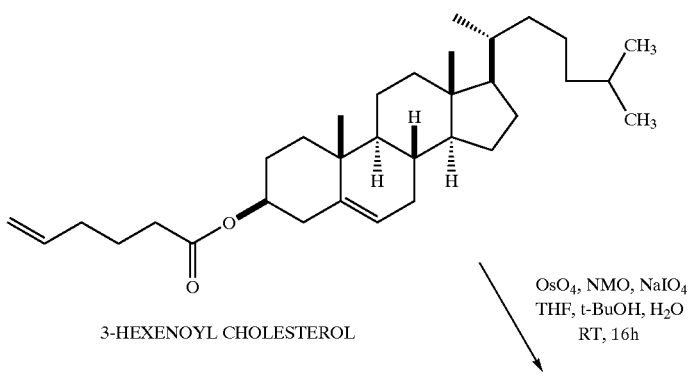

3-HEXENOYL CHOLESTEROL

-continued

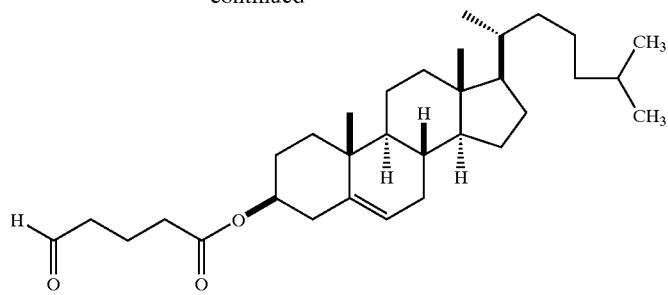

3-ACYL PENTANAL CHOLESTEROL

To a solution of 3-hexenoate of cholesterol (2.0 g, 4.14 mM) in THF and t-BuOH (10 mL each) was added water (5 mL) followed by the addition of NMO (0.97 g, 8.3 mM), NaIO$_4$ (1.78 g, 8.3 mM) and OSO$_4$ solution in t-BuOH (21.3 mg, 0.083 mM) under nitrogen atmosphere. The resulting reaction mixture was stirred for 16 h until complete conversion was observed by TLC analysis. Diatomaceous earth (1.6 g) was added to the reaction mixture and filtered. The filter cake was washed with ethyl acetate (100 mL), and the filtrate was transferred to a separatory funnel and washed with 1N HCl (15 mL), water (25 mL) and brine (15 mL) followed by drying over MgSO$_4$. The filtered solution was evaporated to dryness followed by purification on column chromatography to provide the product in 85% yield. The product was characterized by $^1$H NMR. The NMR analysis revealed that the internal double bond in the cholesterol system was intact for the oxidation conditions.

C. Preparation of Transferrin-3-Cholesterol Conjugate

The aldehyde ester derivative may next be linked with Transferrin to form a Transferrin-3-cholesterol conjugate having a conjugation number n.

1 ml of 1.21 mg (2.5 μmol) 3-acyl-pentanal cholesterol in DMSO was added dropwise to 2 ml of 20 mg (0.5 μmol) Transferrin in PBS-buffer (50 mmol pH 7.0). The reaction mixture was shaken by C24 incubator shaker (New Brunswick Scientific classic series, Edison, U.S.A.) at 37° C. for 30 min. To this was added 0.5 ml of 1.527 mg (25 mmol) ethanolamine PBS solution as a quenching agent to quench the reaction. The turbid mixture was then centrifuged at 1000 g for 10 min at 4°0 C. and the clear supernatant was purified using FPLC on a superdex HR200 column (2.0×30 cm) at 0.5 ml/min of 20 mM Tris-HCl (pH 8.0). The fraction corresponding to Transferrin was collected and dried by lyophilization.

Ill. Ttansferrin-20-Camptothecin Conjugate

Figure 3:
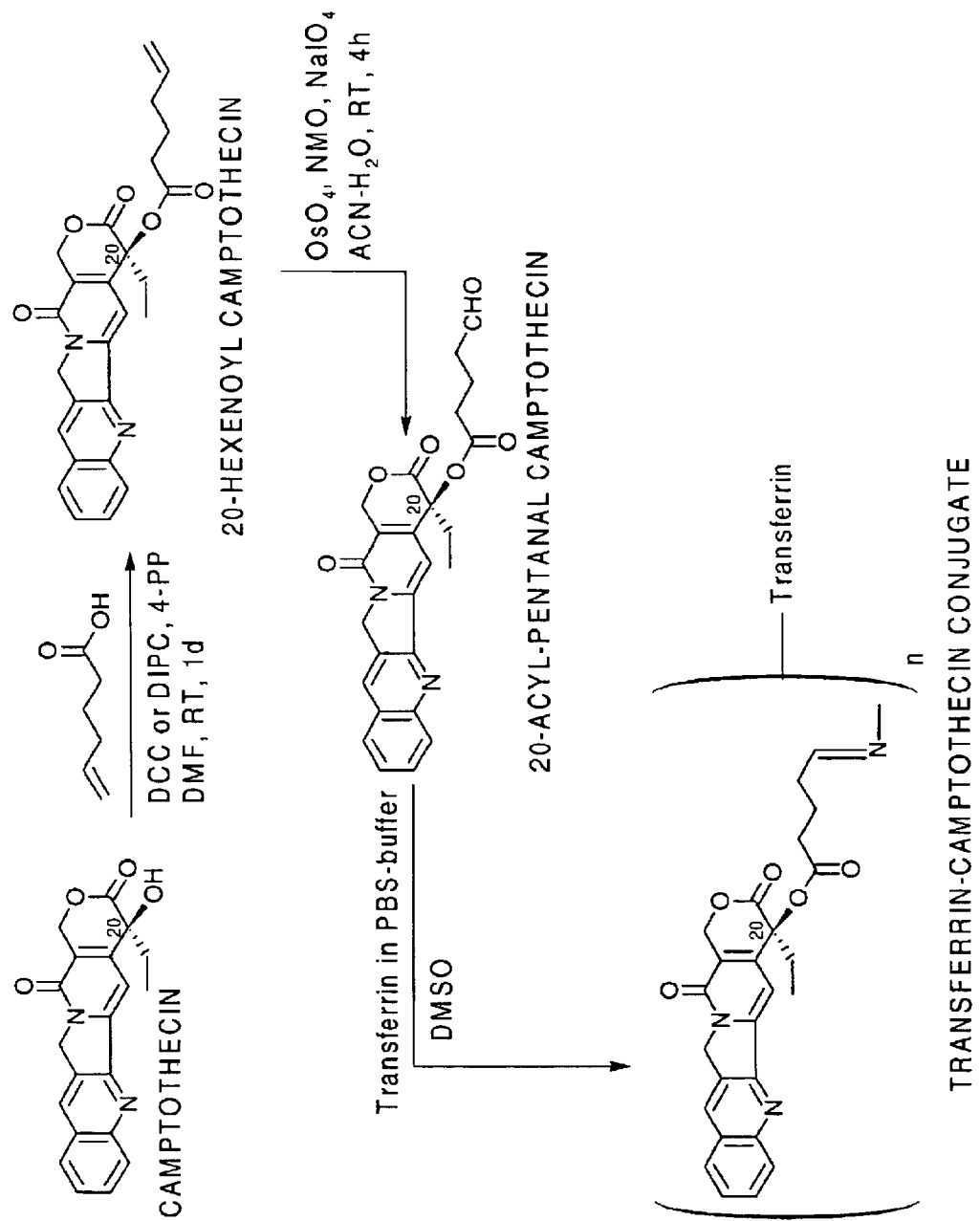
FIG. 3 shows a chemical reaction scheme for forming a Transferrin-20-camptothecin conjugate by linking a 20-acyl-pentanal camptothecin linker compound with Transferrin.

As shown in FIG. 3, camptothecin is first converted through various intermediate compounds to a 20-camptothecin aldehyde ester, which is then linked to Transferrin to form a Transferrin-20-camptothecin conju-

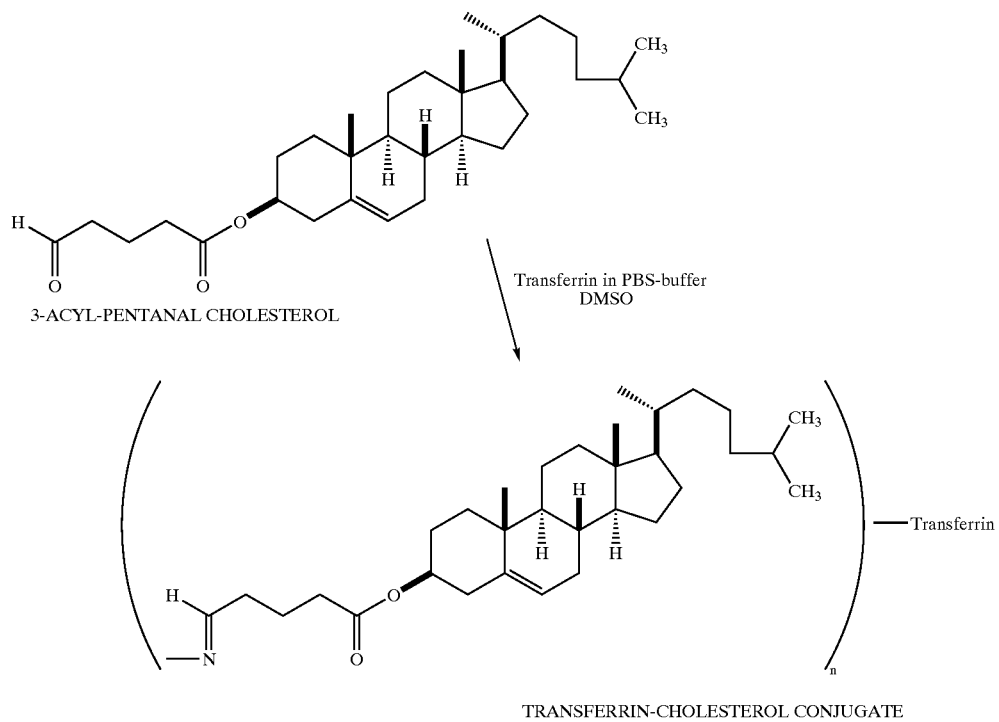

gate. The present invention contemplates that carrier molecules such as other proteins having accessible amino functionalities may be substituted for Transferrin, and other acylating agents as described above may be substituted for 5-hexenoic acid.

A. Preparation of 20-hexenoyl Camptothecin

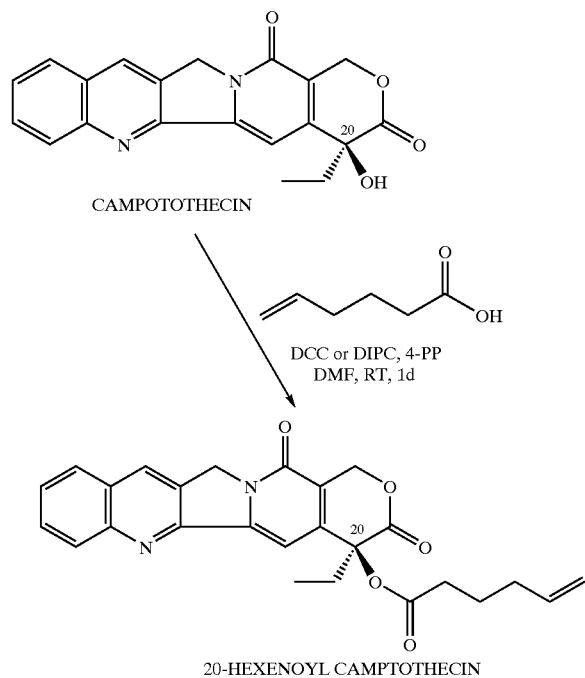

To a mixture of camptothecin (2.0 g, 5.74 mM) and 5-hexenoic acid (0.75 mL, 6.31 mM) in DMF (40 mL) were added DIPC (0.99 mL, 6.31 mM) and 4-PP (0.13 g, 0.86 mM) under nitrogen atmosphere. The resulting reaction mixture was stirred for a period of 24 h at ambient temperatures. After confirmation of complete consumption of camptothecin by TLC analysis, the reaction mixture was transferred to a separatory funnel using methylene chloride and water (200 mL each). The separated organic layer was washed with brine and dried over $MgSO_4$, filtered and evaporated to dryness. The solid residue was crystallized using methylene chloride and ethyl acetate. Crystals were filtered to provide >98% pure material in 70% yield and was characterized by MS and $^1H$ NMR data.

B. Preparation of 20-acyl-pentanal Ester of Camptothecin

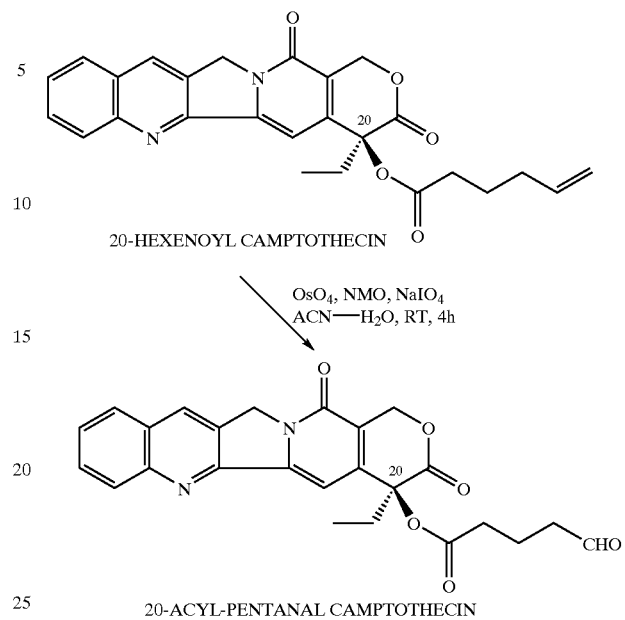

To a solution of 20-hexenoate camptothecin (1.0 g, 2.25 mM) in THF, Acetone and ACN (15 mL each) was added water (15 mL), followed by the addition of NMO (0.53 g, 4.5 mM), $NaIO_4$ (0.96 g, 4.5 mM) and $OSO_4$ (15.3 mg, 0.06 mM) solution in t-BuOH under nitrogen atmosphere. The resulting reaction mixture was stirred at ambient temperatures for 4 h to complete conversion of the hexenoate to the pentanal derivative of camptothecin. The reaction mixture was partitioned between methylene chloride and water (200 mL each). The organic layer was separated and washed with 1N HCl (10 mL), water (50 mL), brine (50 mL) and dried over $MgSO_4$, filtered and evaporated to dryness. The residue was purified by column chromatography and the purified material was characterized by MS and $^1H$ NMR data.

C. Preparation of Transferrin-20-Camptothecin Conjugate

The aldehyde ester derivative may next be linked with Transferrin to form a Transferrin-20-camptothecin conjugate having a conjugation number n.

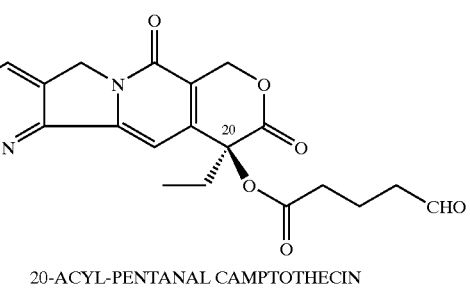

20-ACYL-PENTANAL CAMPTOTHECIN

Transferrin in PBS-buffer
DMSO

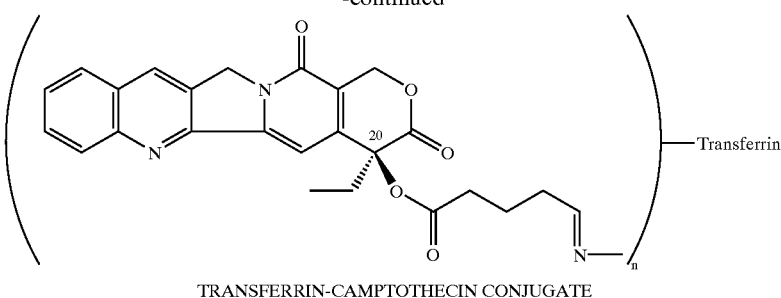

TRANSFERRIN-CAMPTOTHECIN CONJUGATE

The method for forming the Transferrin-20-camptothecin conjugate is similar to the methods for forming the Transferrin-7-paclitaxel conjugate and Transferrin-3-cholesterol conjugate, as described above, which utilize DMSO and Transferrin PBS solution. Mass spectrometry analysis of the resulting Transferrin-20-camptothecin conjugate indicated a coupling ratio of three camptothecin per Transferrin molecule (i.e. n=3). The Circular Dichroism (CD) spectra of Transferrin and of the Transferrin-20-camptothecin conjugate were different, indicating that they might have changed overall conformation.

IV. Transferrin-Rhodamine123 Conjugate

A Transferrin-rhodamine123 conjugate was prepared to utilize the fluorescent properties of rhodamine123 for detection and visualization. The Transferrin-rhodamine 123 conjugate was prepared in a single step using glutaraldehyde as a linker between the free amino groups of rhodamine123 and Transferrin, respectively. An activated aldehyde compound of the formula:

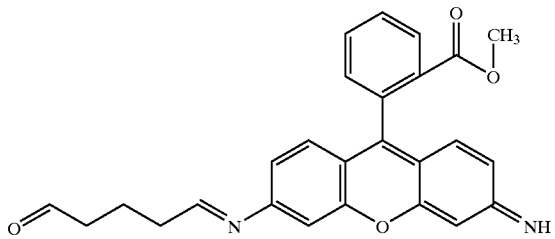

is believed to be formed as an intermediate in this reaction.

I. Preparation of Transferrin-Rhodamine123 Conjugate

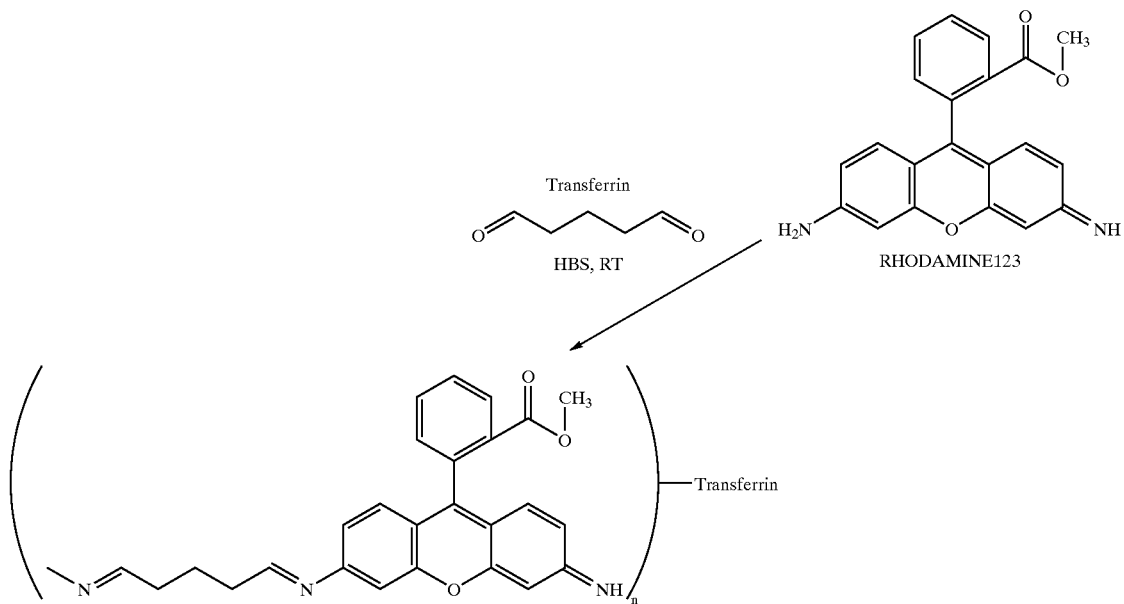

1 ml of 40 mg (0.5 μmol) Transferrin in Hepes-buffer saline (HBS, 150 mmol NaCl, 10 mmol/L Hepes, pH 7.4) was mixed with 1 ml of 5 μmol rhodamine123 by vortexing for 4 min. 1 ml Glutaraldehyde (12.5 mmol in HBS) was added dropwise while vortexing for 4 min at room temperature. The coupling procedure was quenched by adding 0.5 ml of 25 mmol ethanolamine HBS solution as a quenching agent and vortexing for 4 min. The mixture was transferred into dialysis tubing and dialyzed against 1 L of HBS in the dark at 4° C. for 8 h. The turbid mixture was then centrifuged at 1000 g for 10 min at 4° C. and the clear supernatant chromatographed at 0.5 ml/min of 20 mM Tris-HCl (pH 8.0) on a superdex HR200 column (2.0×30 cm). The fraction corresponding to Transferrin was collected and dried by lyophilization.

V. 2'-Paclitaxel Compounds

Figure 4A:
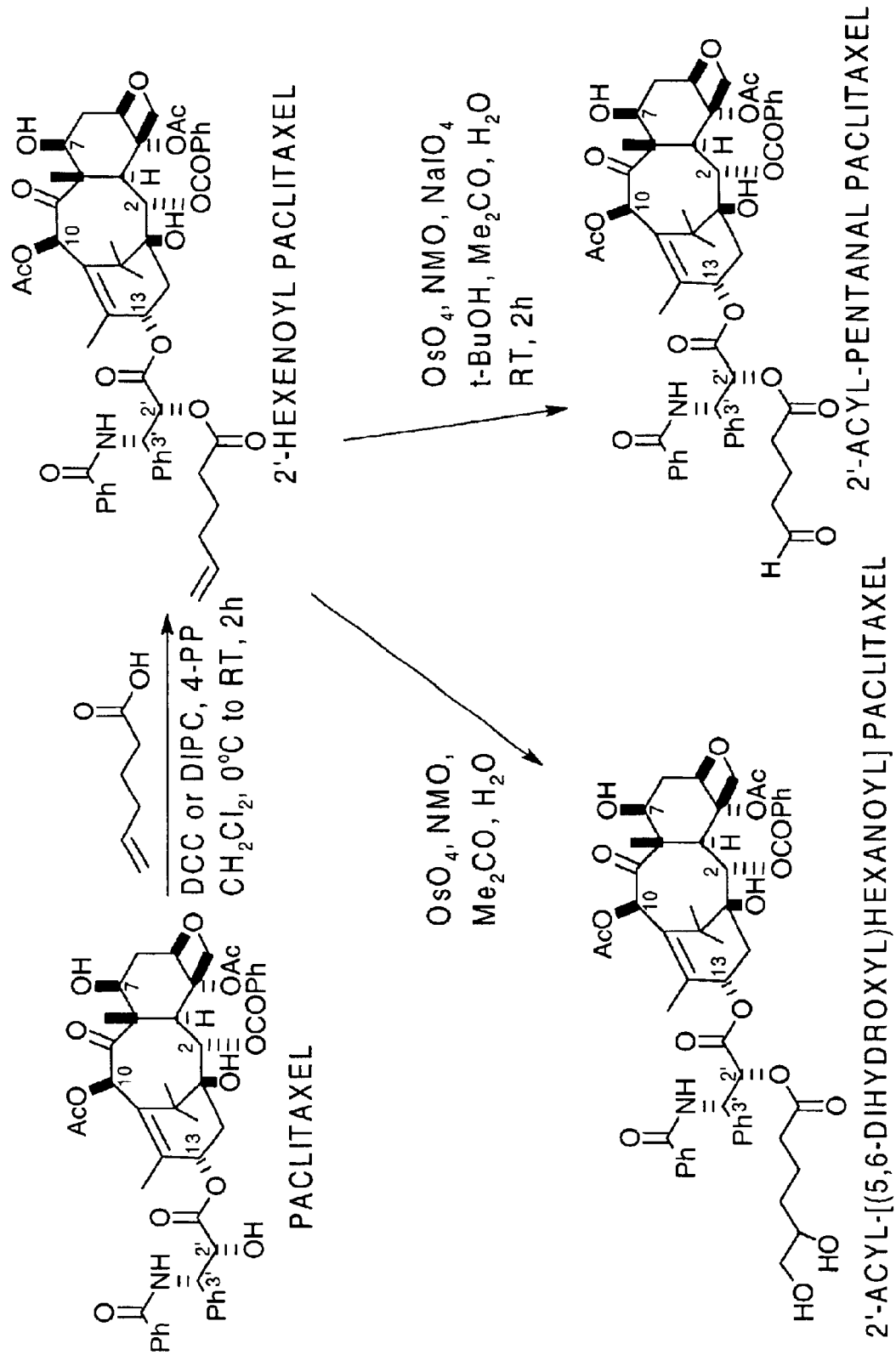
FIG. 4(a) shows a chemical reaction scheme for forming a 2'-acyl-pentanal paclitaxel linker compound for use in forming a Transferrin-2'-paclitaxel conjugate.
Figure 4B:
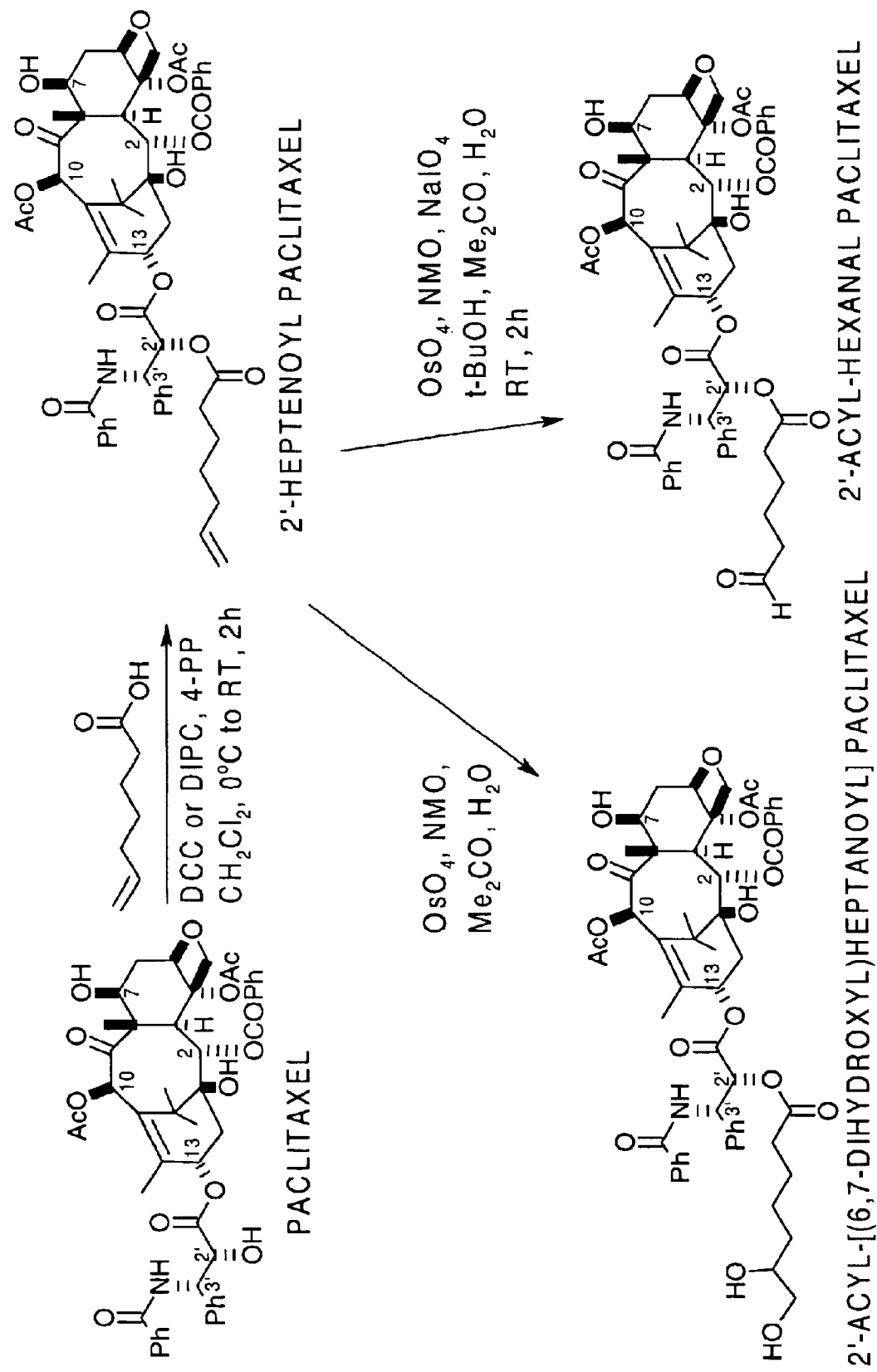
FIG. 4(b) shows a chemical reaction scheme for forming a 2'-acyl-hexanal paclitaxel linker compound for use in forming a Transferrin-2'-paclitaxel conjugate.
Figure 4C:
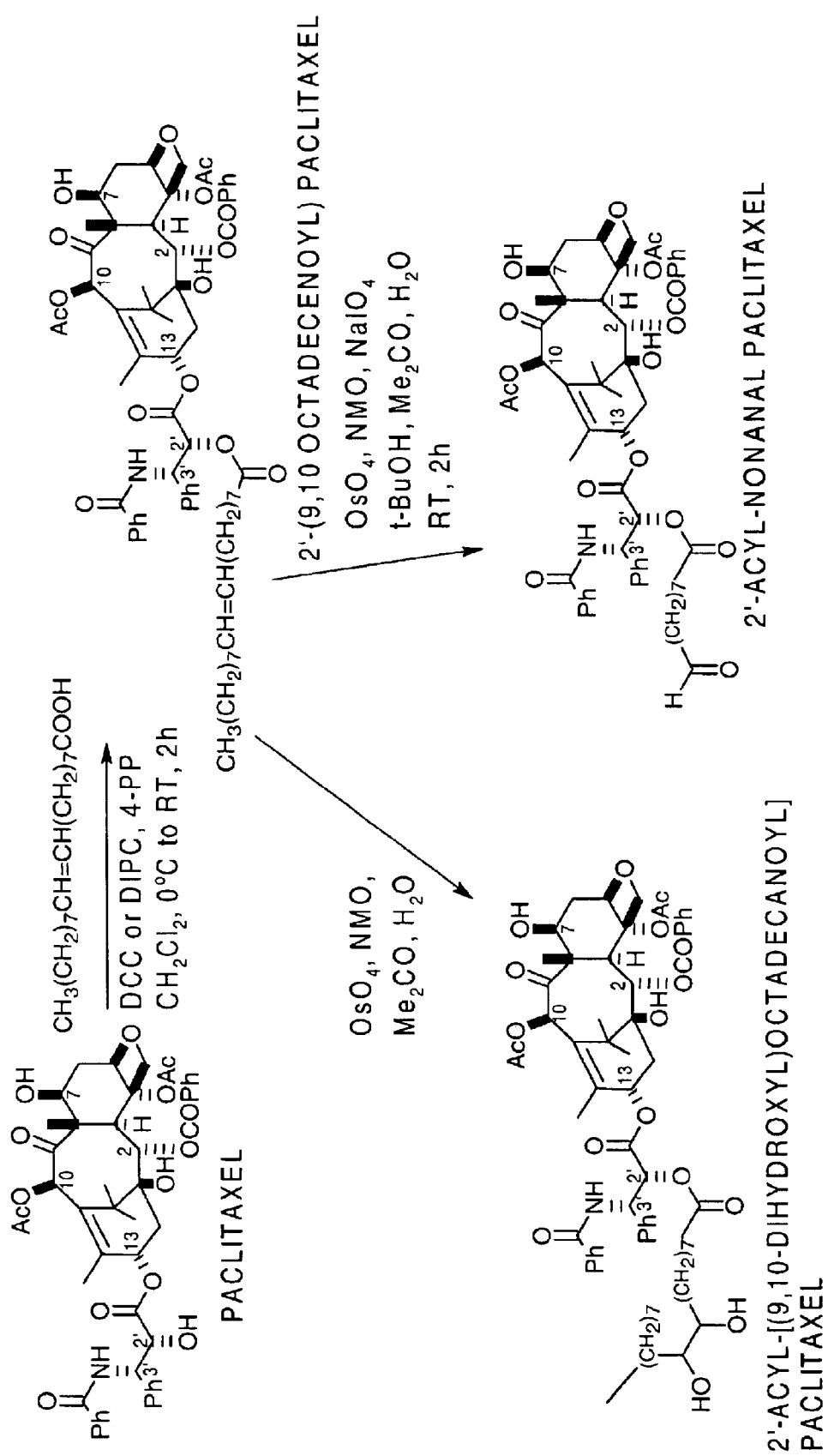
FIG. 4(c) shows a chemical reaction scheme for forming a 2'-acyl-nonanal paclitaxel linker compound for use in forming a Transferrin-2'-paclitaxel conjugate.
Figure 5:
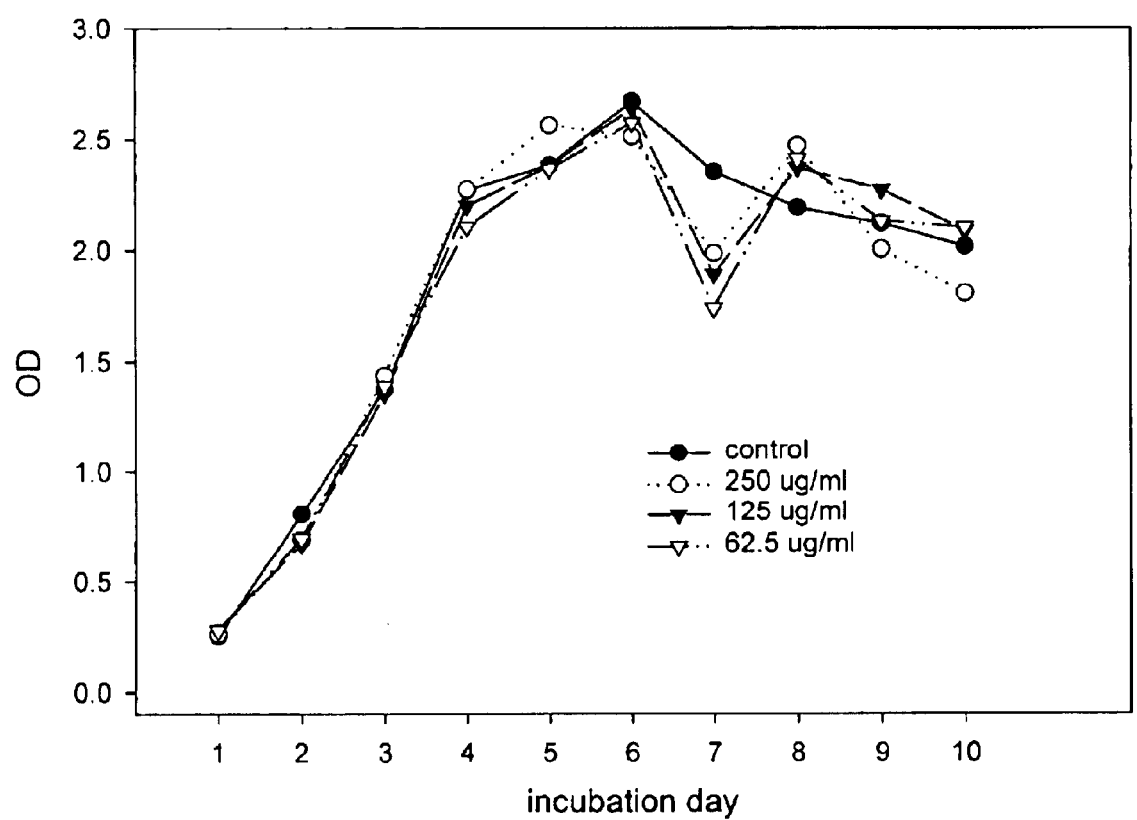
FIGS. 5–7 are graphs demonstrating the cytotoxicity against KB cells of a Transferrin-3-cholesterol conjugate, a Transferrin-rhodamine123 conjugate and a Transferrin-7-paclitaxel conjugate, respectively, at various concentrations under Protocol A.
Figure 6:
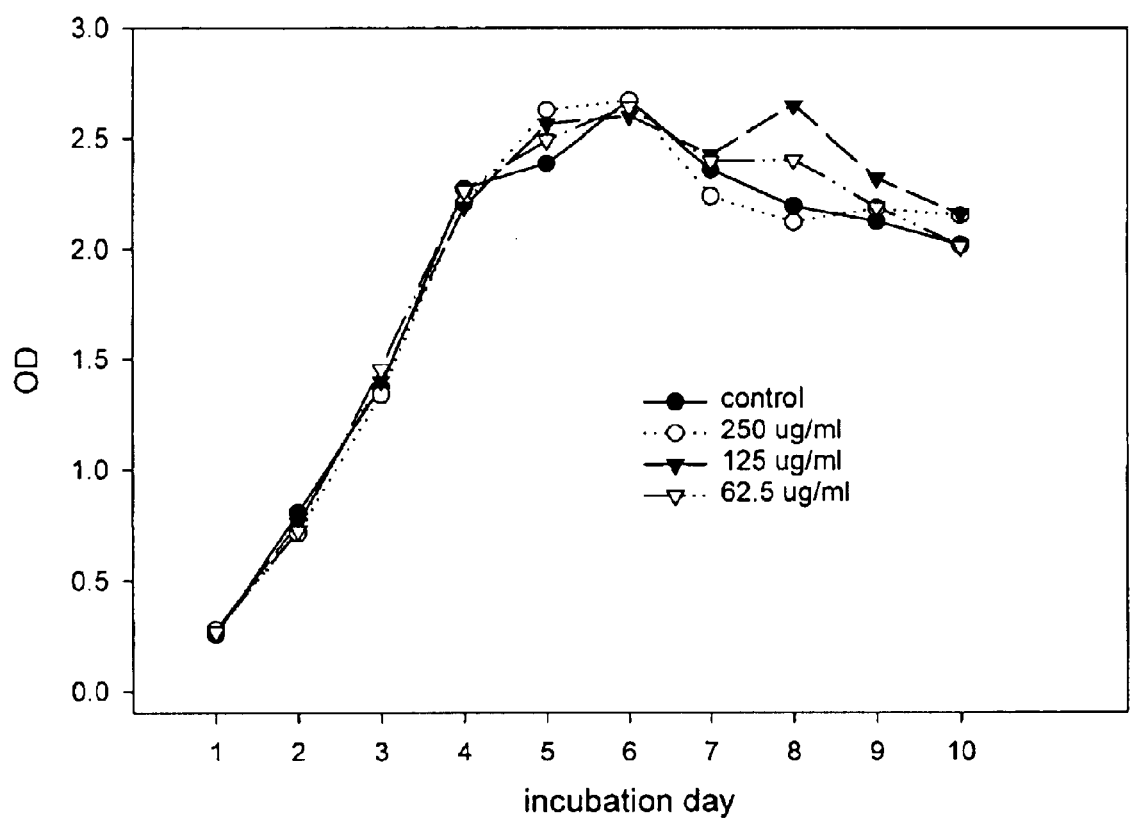

As shown in FIGS. 4(a), 4(b) and 4(c), various 2'-paclitaxel intermediate compounds were formed, although formation of a Transferrin-2'-paclitaxel conjugate was problematic with smaller alkyl-chain aldehyde derivatives (such as using 5-hexenoic acid in the process as in FIG. 4(a)), presumably due to hindrance from the positioning of the 2'-site in the concave region around C-13 of the hemispherical taxane skeleton. Accordingly, this result suggested that a longer alkyl-chain aldehyde derivative, such as one formed using a linking compound having a longer chain than does hexenoic acid, might be utilized to form a Transferrin-2'-paclitaxel conjugate according to the present invention. Further experimentation showed that 2'-heptanal and 2'-nonanal Transferrin conjugates were more readily formed using a similar chemical process, as shown in FIGS. 4(b) and 4(c), respectively. It should be noted that oleic acid (an eighteen carbon chain acid having a double bond at 9,10) was used for the formation of the 2'-nonanal paclitaxel compounds, as shown in FIG. 4(c). Additionally, given that Transferrin is a relatively large protein, this result also suggests that smaller carrier molecules, such as those proteins identified by Safavy, above, may be less hindered by the concave structure of paclitaxel and could conjugate more readily with shorter 2'-paclitaxel alkyl-chain aldehyde derivatives, such as ones where Y<4 in the acylating agent formulas above.

A. Preparation of 2'Hexenoate of Paclitaxel

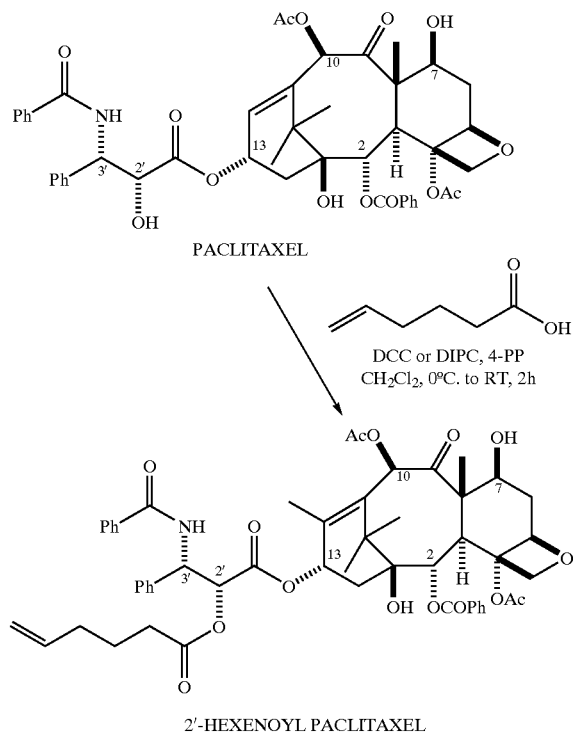

To a solution of paclitaxel (2.0 g, 2.34 mM) and 5-hexenoic acid (0.31 mL, 2.58 mM) in methylene chloride (25 mL) were added DCC (0.72 g, 3.51 mM) followed by 4-PP (0.17 g, 0.5 mM) at 0° C. under nitrogen atmosphere. The resulting reaction mixture was stirred for 2 h, during which time the reaction mixture was brought to ambient temperatures. The reaction was monitored by TLC which confirmed completion of the reaction after 2 h. The mixture was worked up by adding 30 mL each of water and ethyl acetate. The mixture was transferred to a separatory funnel and the organic layer was washed with 1N HCl (10 mL), water (30 mL) and brine (20 mL) and dried over magnesium sulfate. The filtrate after drying was evaporated to dryness and crystallized with methyl t-butyl ether. The resulting compound was >95% pure by HPLC and $^1$H NMR analysis confirmed the esterification at the 2'-hydroxyl of the paclitaxel without affecting the 7-hydroxyl thereof. Yield was 98%.

B. Preparation of 2' Aldehyde Derivative of Paclitaxel

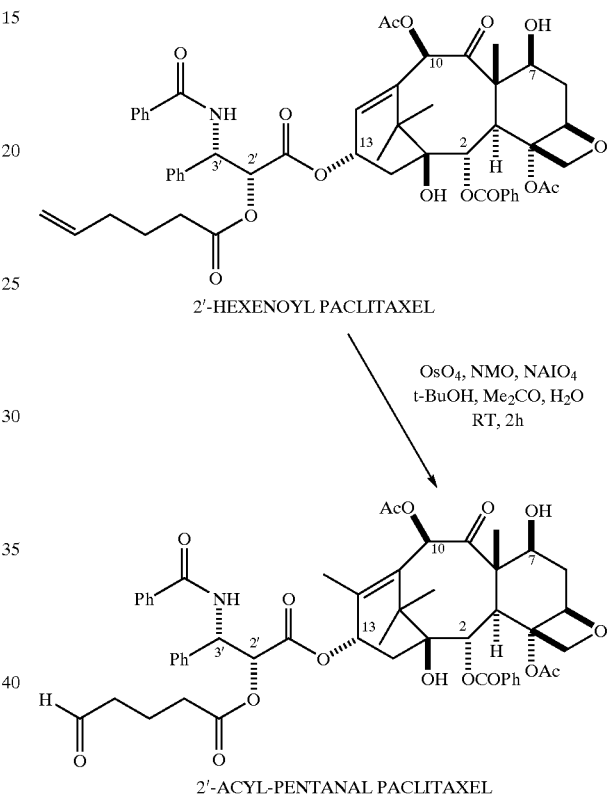

To a solution of 2'-hexenoate of paclitaxel (0.475 g, 0.5 mM) in t-BuOH, acetone and water (2 mL each) were added NMO (0.118 g, 1 mM), NaIO$_4$ (0.214 g, 1 mM) and OSO$_4$ (2.54 mg, 0.01 mM) solution in t-BuOH under an atmosphere of nitrogen. The resulting mixture was stirred at ambient temperatures for 2 h and at this time, TLC showed completion of the reaction. The mixture was worked up by adding water and ethyl acetate (20 mL each), the organic layer was separated and washed with 1N HCl (10 mL), water (10 mL) and brine (10 mL). The organic layer was filtered over magnesium sulfate and sodium hydrosulfite and evaporated to dryness. The crude compound was purified by column chromatography using ethyl acetate and heptane, which was characterized by MS and $^1$H NMR. Yield: 85%

C. Preparation of 2' Diol Derivative of Paclitaxel

As shown in FIG. 4(a), when NaIO$_4$ was not used in the above reaction, the diol was isolated, as follows:

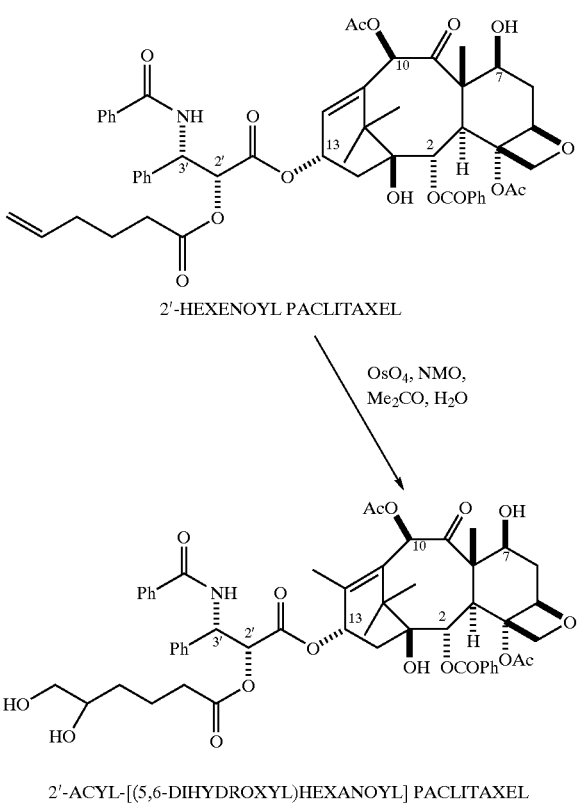

2'-HEXENOYL PACLITAXEL

OsO₄, NMO, Me₂CO, H₂O

2'-ACYL-[(5,6-DIHYDROXYL)HEXANOYL] PACLITAXEL

To a solution of the 2'-hexenoate of paclitaxel (9.0 g, 9.47 mM) in acetone (135 mL) was added water (50 mL). To the resulting solution was added NMO (2.22 g, 18.94 mM) followed by $OsO_4$ solution in t-BuOH (48.2 mg, 0.19 mM) under an atmosphere of nitrogen and left stirring for 16 h. After confirming completion of the conversion by TLC, diatomaceous earth (15 g) was added to the reaction mixture and filtered. The filtrate was evaporated free of acetone on the rotavapor followed by extraction with ethyl acetate (200 mL) after saturating the aqueous layer with solid NaCl. The resulting organic layer was washed with water (10 mL), 1N HCl (100 mL), water (10 mL) and brine (100 mL) and filtered through $MgSO_4$. The solvent was evaporated to a residue which was purified by column chromatography to yield the pure diol in 65% yield. As with the corresponding diol of the 7-paclitaxel derivative discussed above, the oxidative cleavage of the diol on treatment with $NaIO_4$ provides the terminal aldehyde.

D. Preparation of Transferrin-2'-acyl-hexanal Paclitaxel Conjugates

As shown in FIG. 4(b), paclitaxel was first converted to a 2'-acyl-hexanal paclitaxel compound through various intermediates. The chemistry for forming the 2'-acyl-hexanal paclitaxel aldehyde ester derivative is similar to that described above with respect to forming the 2'-acyl-pentanal paclitaxel derivative, except that 6-heptenoic acid is used in place of the 5-hexenoic acid.

The aldehyde ester is then linked to Transferrin to form a Transferrin-2'-paclitaxel conjugate having conjugation number n as follows:

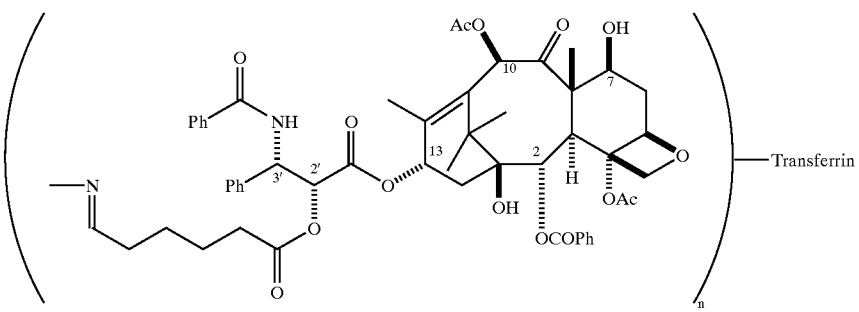

The procedure was similar to that described above with respect to the preparation of a Transferrin-7-paclitaxel conjugate. Mass Spectrometry revealed that the major Transferrin-2'-paclitaxel conjugate product had a coupling ratio of one paclitaxel molecule per Transferrin (i.e. n=1), although conjugates with two paclitaxel molecules to each Transferrin (i.e. n=2) were also detected. Circular dichroism spectra of Transferrin and the Transferrin-2'-paclitaxel conjugate in the far UV region were different, indicating that the 2'-paclitaxel conjugates might have a changed overall conformation.

E. Preparation of Transferrin-2' Acyl-nonanal Paclitaxel Conjugate

As shown in FIG. 4(c), a Transferrin conjugate of 2'-paclitaxel was formed by first converting paclitaxel to a 2'-acyl-nonanal paclitaxel aldehyde ester compound through various intermediates. While the chemistry is again similar to that described above with respect to the 2'-acyl-pentanal paclitaxel derivative, it should be noted that oleic acid (cis-9-octadecenoic acid: $CH_3(CH_2)_7CH=CH(CH_2)_7CO_2H$) was used as the acylating agent, as shown in FIG. 4(c). Accordingly, when the chain was cleaved to form the aldehyde, that portion of the chain extending beyond the 9,10 double bond was removed.

The conjugation of the 2'-acyl-nonanal paclitaxel with Transferrin to form a Transferrin-2'-paclitaxel conjugate of the following formula:

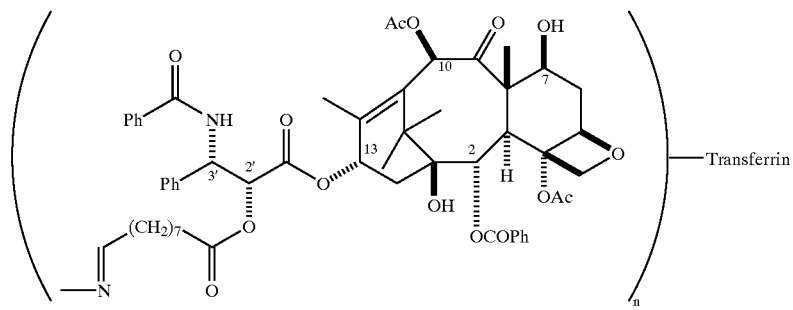

was similar to that described above with respect to the Transferrin-7-paclitaxel conjugate.

VI. Amido Derivatives

The present invention also contemplates the formation of amido-derivatives of amine-bearing compounds. For example, a paclitaxel analog of the formula:

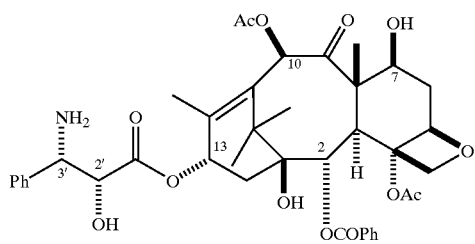

could be coupled with an appropriate acylating agent, preferably having a terminal olefin, thereby to form an amido derivative of paclitaxel that can be converted into an aldehyde linker for use with Transferrin or other carrier molecules/proteins. An exemplary intermediate formed by coupling the above amine-bearing paclitaxel analog with hexenoic acid is as follows:

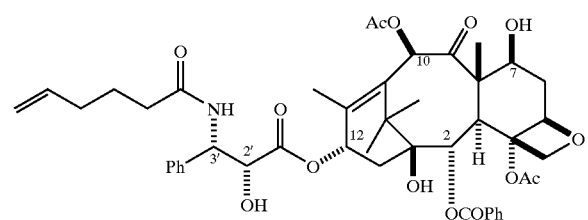

Such an intermediate could be converted to the corresponding diol:

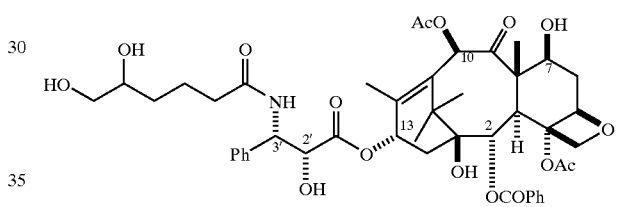

and the aldehyde:

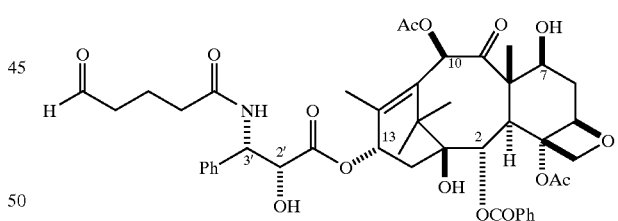

according to the processes disclosed above with respect to the 7-paclitaxel and 2-paclitaxel derivatives, for example. A Transferrin conjugate of the formula:

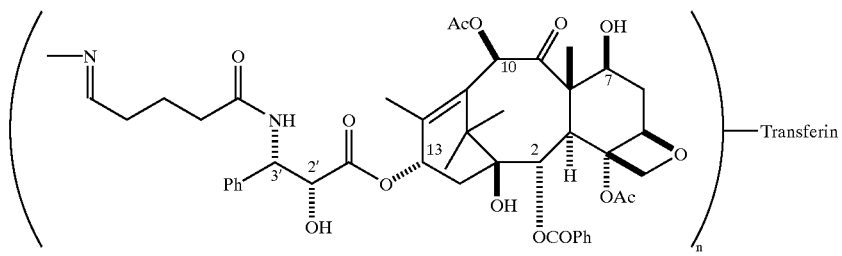

is accordingly contemplated. The use of linking compounds having a longer chain length than hexenoic acid is contemplated to address any difficulties with forming the Transferrin conjugate due to hindrance from positioning of the side chain in the concave region around C-13 of the hemispherical taxane skeleton. For example, the use of heptenoic acid resulted in the formation of a Transferrin conjugate of the formula:

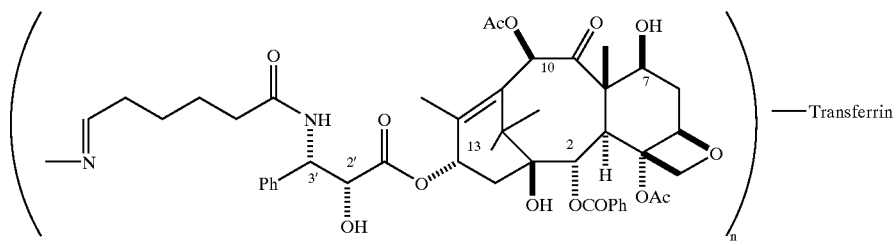

Here, a protected taxane was first converted to its corresponding amine-hydrochloride salt, as follows:

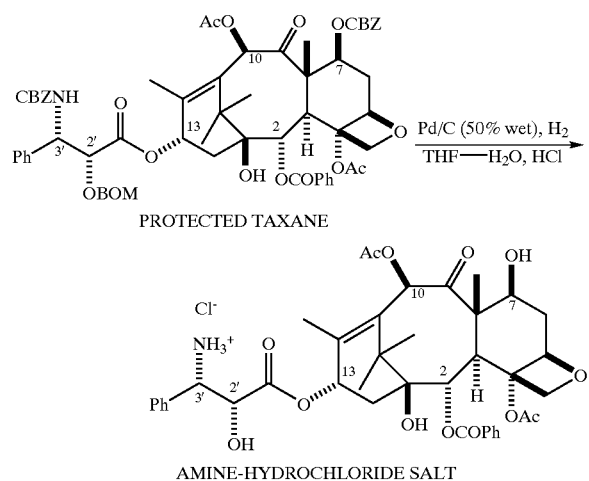

PROTECTED TAXANE

AMINE-HYDROCHLORIDE SALT

The formation of such a protected taxane, such as the 7-O,3'-N-di-(CBZ)-2'-O—BOM paclitaxel shown in the formula above, is known in the art and is disclosed, for example, in U.S. Pat. Nos. 5,750,737; 5,973,170; 6,133,462; 6,066,749; 6,048,990; 6,136,999; and 6,143,902, the teachings of which are incorporated herein by reference. The formation of the amine-hydrochloride salt shown in the reaction above is described more fully in U.S. patent application Ser. No. 09/843,284, now U.S. Pat. No. 6,479,679, the teachings of which are also incorporated herein by reference.

For example, in an exemplary reaction, 5.05 g of 7-O,3'-N-di-(CBZ)-2'-O—BOM paclitaxel was dissolved in 90.0 mL of THF in an 0.5L round bottom flask equipped with a magnetic stir bar, to which was added 6.01 mL of 3.62M hydrochloric acid (22.08 mmol) and 8.10 g of 10% Pd/C 50% wet. The reaction vessel was flushed three times with nitrogen and two times with hydrogen, and the reaction mixture was stirred vigorously under an atmosphere provided by a hydrogen filled balloon for about one hour at room temperature. This results in the amine-hydrochloride salt shown in the reaction above. It should be appreciated that other mineral acids, as well as organic acids, may be used in place of the hydrochloric acid used in the above process.

Other processes are known for forming the ammonium salts of taxanes. For example, the use of trifluoroacetic acid to form the corresponding ammonium trifluoroacetate (TFA) salt is disclosed, for example, in U.S. Pat. Nos. 5,675,025; 5,684,175; 5,770,745; 5,939,566; 5,948,919; 6,048,990; 6,066,749; 6,072,060; 6,136,999; 6,143,902; 6,262,281; and 6,307,088, the teachings of which are incorporated herein by reference.

Once the amine-hydrochloride acid salt was formed, it was then reacted with heptenoic acid to form the corresponding heptenoate as follows:

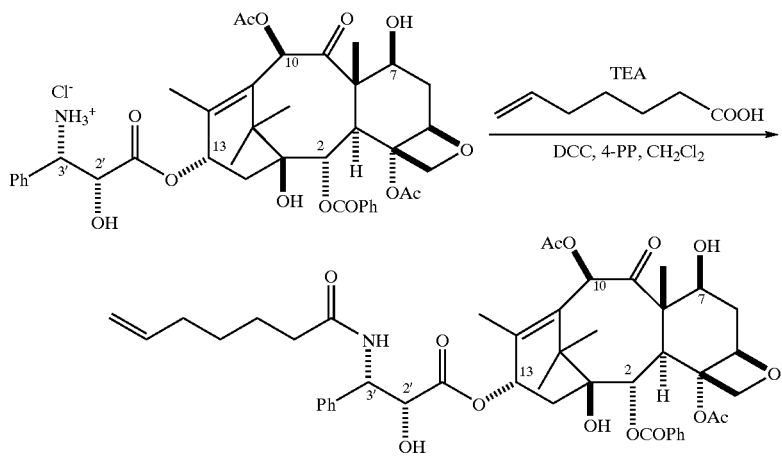

This reaction is generally similar to those disclosed above with reference to 7-paclitaxel derivatives or 2'-paclitaxel derivatives, except that it should be appreciated that triethylamine (TEA) is added to free the amine salt to its corresponding free amine. The resulting heptenoate was then converted to the corresponding 3'-amido-hexanal paclitaxel as follows:

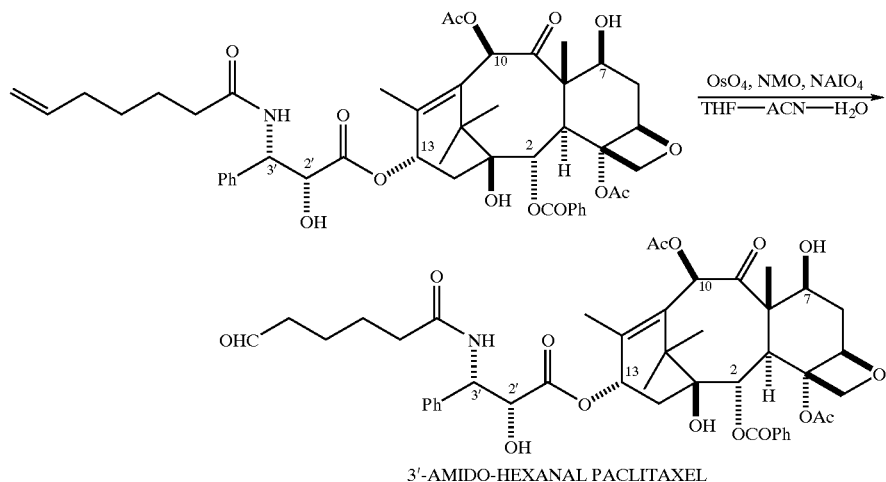

3'-AMIDO-HEXANAL PACLITAXEL

This reaction is again similar to that described with reference to other derivatives, above. The resulting aldehyde was then linked with Transferrin using a procedure similar to that described above with respect to forming the Transferrin-7-paclitaxel conjugates to provide the Transferrin-3'-amido-hexanal paclitaxel conjugate. The circular dichroism spectra of Transferrin and of the Transferrin-3'-amido-hexanal paclitaxel conjugate were similar, indicating that they had a similar overall conformation.

It should be appreciated from the foregoing that the corresponding free amine itself can be used in place of the amine salt. The formation of the free amine of taxanes is disclosed, for example, in U.S. Pat. Nos. 5,688,977; 5,770,745; 5,939,566; 6,048,990; 6,066,749; 6,072,060; 6,107,497; 6,262,281; and 6,307,088, the teachings of which are incorporated herein by reference. Accordingly, the present invention contemplates substituting for the amine-hydrochloride salt in the example above compounds of general formula:

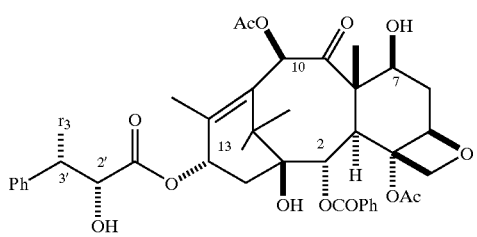

and their analogs and derivatives, where $R_3$ can be $NH_2$ or $NH_2HA$ where HA is an organic acid or mineral acid.

VII. Generalized Procedures and Compounds

As apparent from the foregoing discussion, the present invention lends itself to a generalized procedure for forming protein-drug conjugates. A hydroxyl-bearing or amino-bearing biologically active compound, or an analog or derivative thereof, of the formula $R_1$—$NH_2$ or $R_1$—OH is first provided, which may optionally be protected by one or more protecting groups on other positions to the extent known in the art. It should also be appreciated that the present invention contemplates secondary amines of the amino-bearing biologically active molecules (i.e. of formula $R_1R_4NH$, where $R_4$ is any appropriate radical as known in the art).

The biologically active compound is reacted with a compound selected from the formulas:

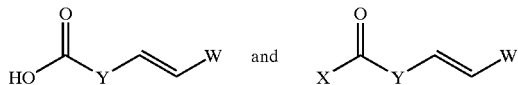

wherein W, X and Y are as described above, thereby to form a compound having the formula:

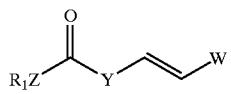

where Z is —O— when the biologically active compound is of the formula $R_1$—OH and Z is —NH— where the biologically active compound is of the formula $R_1$—$NH_2$, and W and Y are as above. This compound is oxidized to an aldehyde of the formula:

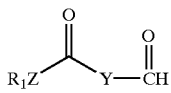

Alternatively, the corresponding diol of formula:

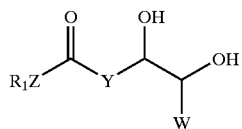

may be formed as an intermediate that may be cleaved to the aldehyde. The aldehyde is linked with a protein or other carrier molecule having accessible amino functionalities, such as a compound of a generalized formula:

$(NH_2)_m$—P where m is an integer, P is a protein or other carrier molecule, and $(NH_2)_m$ are the accessible amino functionalities thereof, thereby to form a conjugate of the formula:

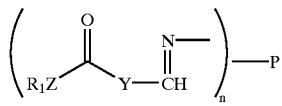

wherein n is the conjugation number of the molecular conjugate, which reflects the number of molecules of a given drug that are linked to a single carrier molecule, and which may vary based on the reaction conditions and underlying intermediate compounds used to link a given drug to a carrier molecule, such as a Transferrin protein.

Carrier molecules contemplated for use in the present invention include proteins such as Transferrin, the receptor ligand peptides recognized by Safavy, or other proteins, antibodies, lectins or other substances that may become attached to the surface of a cell.

It should also be appreciated that this generalized procedure contemplates the formation of various intermediate compounds, such as the olefins, diols and aldehydes of general formula:

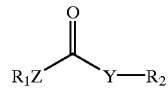

wherein $R_1$, Z and Y are as above and $R_2$ is —CH=CH(W), —CH(OH)CH(OH)W, or —C(O)H, where W is as above. As appropriate, $R_1$ may include one or more protecting groups, such as TBDMS, TROC, BOM, benzyl, TES or EE in the case of paclitaxel, for example. In such case, the method may include steps of protecting and deprotecting $R_1$, as appropriate, with one or more protecting groups. For example, paclitaxel may be protected at the 2' site with TBDMS, TROC, BOM, benzyl, TES or EE, or the like, prior to the step of coupling it with the acylating agent, and may thereafter be deprotected at 2' after the step of converting the compound to its corresponding aldehyde.

VIII. Analysis/Characterization

Transferrin-drug conjugate products formed according to the above-described methods were characterized by mass spectrometry and FPLC. UV Spectra were collected from 200 nm to 800 nm. The concentrations of the Transferrin/Transferrin conjugates were 0.5 mg/ml. Samples were prepared in PBS (pH=7.4) buffer. Circular dichroism experiments were carried out by collecting spectra from 240 nm to 190 nm with a cylindrical quartz cell of path length 1 mm. The concentrations of the Transferrin/Transferrin conjugates were 1 mg/ml. Samples were prepared in $H_2O$ or PBS (pH=7.4) buffer.

The Transferrin, rhodamine123 and Transferrin-rhodamine123 conjugate were evaluated using a fluorescence spectrofluorophotometer. The Transferrin (0.25 mg/ml), rhodamine123 (10 ng/ml) and Transferrin-rhodamine123 conjugate (0.25 mg/ml) were dissolved in phosphate buffer (pH 7.0). The excitation wavelength was 280 nm for Transferrin and Transferrin-rhodamine123 conjugate, 500 nm for rhodamine123, and emission spectra were recorded in the range of 300 to 700 nm.

The gel-electrophoresis technique of Laemmli ("Cleavage of Structural Proteins During the Assembly of the Head of Bacteriophage T4", Nature, 227, 680–685 (1970)) was used to assess the purity of the Transferrin conjugates. Sodium dodecyl sulphate (SDS) polyacrylamide gel electrophoresis of the conjugate column fractions were performed with a vertical slab gel composed of 12% acrylamide (NuPAGE electrophoresis system, NOVEx®) and run in a E1900-XCELL™ Mini Cell (Novex, San Diego, Calif.) apparatus. Samples were prepared and loaded on the gel after heating at 100° C. for 3 min. The Transferrin conjugates (20 µl) were loaded on the gel at approximately 0.03 mg/ml protein. When the electrophoresis was completed, the gels were stained for 30 min with Coomassie blue stain solution and then destained for 5–12 h. In the case of the Transferrin-7-paclitaxel conjugate, samples were analyzed in presence and absence of 2-mercaptoenthanol (1 µl, a reducing reagent).

The standard curve of paclitaxel by HPLC was obtained by injection of known quantities of paclitaxel and plotting the peak area vs concentration of paclitaxel. The sample was analyzed by analytical reversed-phase HPLC using a C-4 column (5 µm, 300 Å, 25 cm×4.6 mm i.d., flow rate 1 ml/min) eluting gradient of solvent A, 80% $H_2O$: 20% ACN: 0.1% TFA, and solvent B, 80% ACN: 20% $H_2O$: 0.1% TFA.

The total HPLC analysis run was 24 min. The gradient method used for the analytical HPLC was started from solvent B from 0% to 100% over 20 min, followed by elution at 100% of solvent B for 2 min. Finally, a gradient change back to 0% solvent B was done over 2 min.

Stock solution (1 mg/ml) of paclitaxel was prepared by dissolving paclitaxel in EtOAc. The final concentrations of paclitaxel were 25, 50, 75, 100 µg/ml. For each concentration, sample was injected into HPLC in duplicate and the standard curve of paclitaxel was obtained by plotting the averaged peak area vs concentration of paclitaxel.

The coupling ratio of the Transferrin-7-paclitaxel conjugate was measured after an acid hydrolysis of the conjugate followed by measurement of the paclitaxel by HPLC. 1 mg Transferrin-paclitaxel was dissolved in 0.4 ml PBS buffer, pH was adjusted to 4 by adding acetic acid and the reaction mixture was stirred at room temperature for 10 min. Paclitaxel was isolated by adding 0.2 ml EtOAc into reaction mixture and vortexing for 2 min. The turbid mixture was then centrifuged at 1000 g for 10 min at 4° C. and the clear supernatant 20 µl that contained paclitaxel was injected into HPLC. According to the standard curve of paclitaxel, there was a coupling ratio of 3 paclitaxel per Transferrin.

IX. Stability of the Transferrin Conjugates

A. Thermal Stability

Stock solutions of Transferrin and Transferrin conjugates were prepared by dissolving Transferrin and Transferrin conjugates (1 mg/ml) in PBS buffer (pH 7.0, 0.05 mol). Aliquoted 0.1 ml into sealed tubes and incubated at 37° C. At appropriate time intervals, aliquots were removed in triplicate, frozen immediately in dry ice and stored at −70° C. until analysis by CD and SDS-PAGE Electrophoresis. Immediately prior to analysis the appropriate sample was fast-thawed.

B. pH-Dependent Stability

Stock solutions of Transferrin and Transferrin conjugates were prepared by dissolving Transferrin and Transferrin conjugates (1 mg/ml) in $H_2O$. The stock solutions were further diluted in different pH buffer (0.05 mol) and the final concentration was 0.1 mg/ml. Samples were incubated at room temperature for 2 h, or at 37° C. for 2 h analysis by CD, Fluorescence and UV Spectroscopy.

X. Cytotoxicity Data

The growth inhibitory potential of the Transferrin-3-cholesterol conjugate, the Transferrin-rhodamine123 conjugate and the Transferrin-7-paclitaxel conjugate with cultured mammalian cells was investigated. As discussed below, the Transferrin conjugates of rhodamine123 and cholesterol did not demonstrate significant adverse effect against either tumor or normal cells. This demonstrates that conjugation of substances to Transferrin by itself is not sufficient to cause effect on cell growth. However, the conjugate of paclitaxel, a compound exhibiting efficacy against cancer, showed promise in targeting cancer cells while not adversely affecting normal cells. Thus, the present invention suggests a promising route to specifically target cancer cells with compounds that exhibit efficacy in cancer treatment, with the potential of not harming normal cells at optimal doses.

The cell lines selected were KB (human epidermoid carcinoma in the mouth, ATCC #CCL-17), Lu-1 (human lung cancer cell lines, obtained from the Department of Surgical Oncology, University of Illinois, College of Medicine), and hTERT (telomerase-immortalized normal epithelial cell line, Clontech #C4000-1). Various doses of the compounds were evaluated under two treatment protocols. In Protocol A, cultures of each of the KB, Lu and hTERT cells were treated with various doses of the three conjugate compounds from the day of culture onward. In Protocol B, cultures of each of the KB, Lu and hTERT cells were grown to confluence (9 days), and then treated with various doses of the Transferrin-7-paclitaxel conjugate for the duration of the experiment.

KB was cultured in DMEM (GIBCO) supplemented with 10% fetal bovine serum (FBS), 100 units/ml penicillin G, 100 µg/ml streptomycin sulfate, 0.25 µg/ml amphotericin B (Fungizone) (PSF) (GIBCO) and 1% non-essential amino acids (NAA) (Sigma). Lu was maintained in MEME (GIBCO) supplemented with 10% FBS, PSF, and 1% NAA. hTERT-RPE1 was maintained in DMEM/F-12 (GIBCO) supplemented with 10% FBS+PSF. All cell lines were cultured at 37° C. in 100% humidity with a 5% $CO_2$ atmosphere in air.

The overall procedures were those as described by Skehan et al., New calorimetric cytotoxicity assay for anticancer-drug screening, *J. Natl. Cancer Inst.* 82:1107–1112, 1990, and Likhitwitayawuid et al., Cytotoxic and antimalarial bisbenzylisoquinoline alkaloids from *Stephania erecta*. *J. Nat. Prod.* 56:30–38, 1993. Cells were typically grown to 60–70% confluence, the medium was changed, and the cells were used for test procedures one day later. Test samples were initially dissolved in sterilized PBS. Serial dilutions were performed using PBS as the solvent, and 10 µl were added to the three wells. PBS (10 µl) was added to control groups. After the plates were prepared, cells were removed from the tissue culture flasks by treatment with trypsin, enumerated, and diluted with fresh media. KB ($3 \times 10^4$ cells/ml), Lu ($5 \times 10^4$ cell/ml) and hTERT-RPE1 ($4 \times 10^4$ cells/ml) cells (in 190 µl of media) were added to the 96-well plates. The plates were incubated at 37° C. in 5% $CO_2$, the cells fixed by addition of 100 µl of cold 20% trichloroacetic acid and incubated at 4° C. for 30 min. The plates were washed with tap water (3×) and dried overnight. The fixed cells were stained 30 min by the addition of 100 µl of 0.4% sulforhodamine B (w/v) dissolved in 1% acetic acid. The plates were washed with 1% acetic acid (3×) and allowed to dry. The bound dye was solubilized by the addition of 10 mM unbuffered Tris base, pH 10 (200 µl/well). The plates were placed on a shaker for 5 minutes, and the absorption was determined at 515 nm using an ELISA plate reader. In each case, a zero-day control was performed by adding an equivalent number of cells to several wells of the 96-well plates and incubating at 37° C. for a period of 30 min. The cells were then fixed with tichloroacetic acid and processed as described above.

Figure 7:
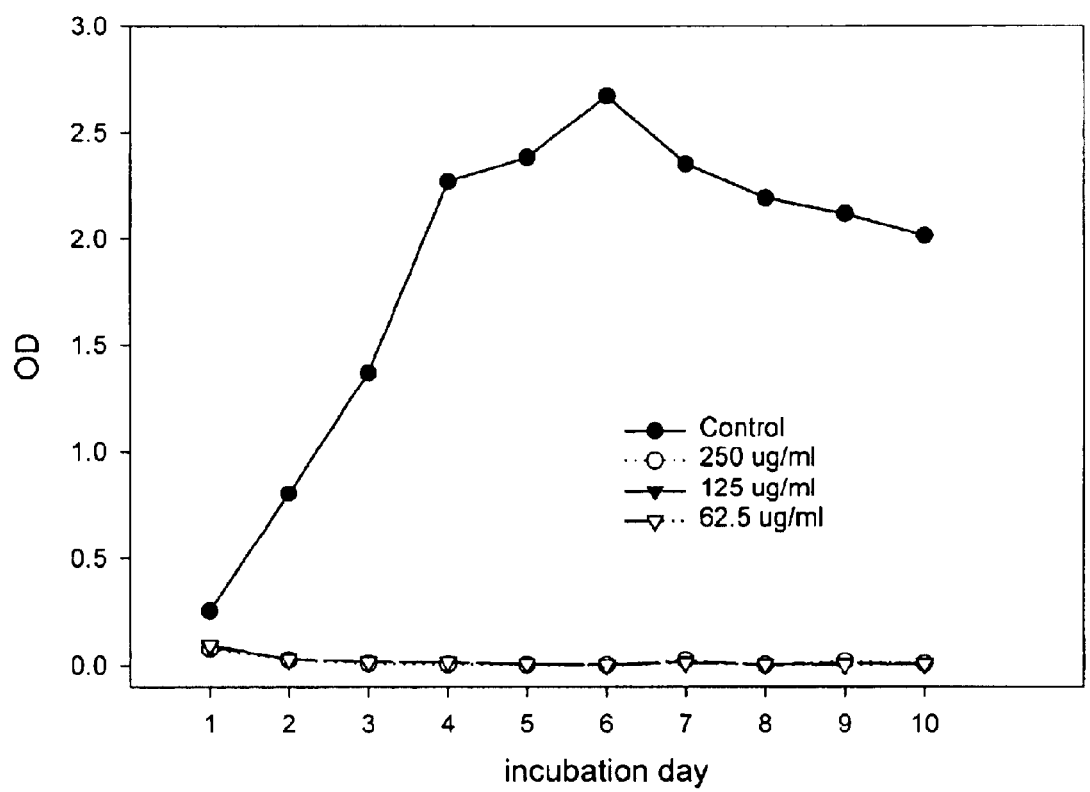
Figure 8:
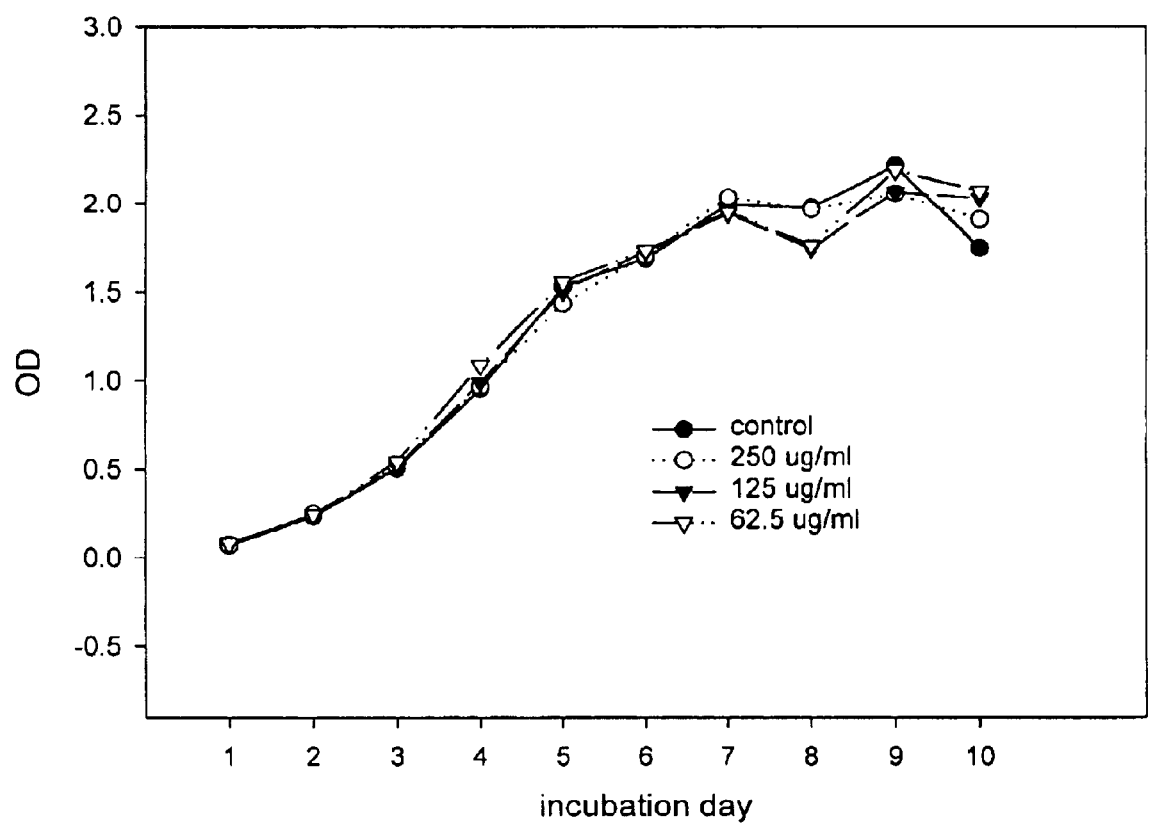
FIGS. 8–10 are graphs demonstrating the cytotoxicity against Lu cells of a Transferrin-3-cholesterol conjugate, a Transferrin-rhodamine123 conjugate and a Transferrin-7-paclitaxel conjugate, respectively, at various concentrations under Protocol A.
Figure 9:
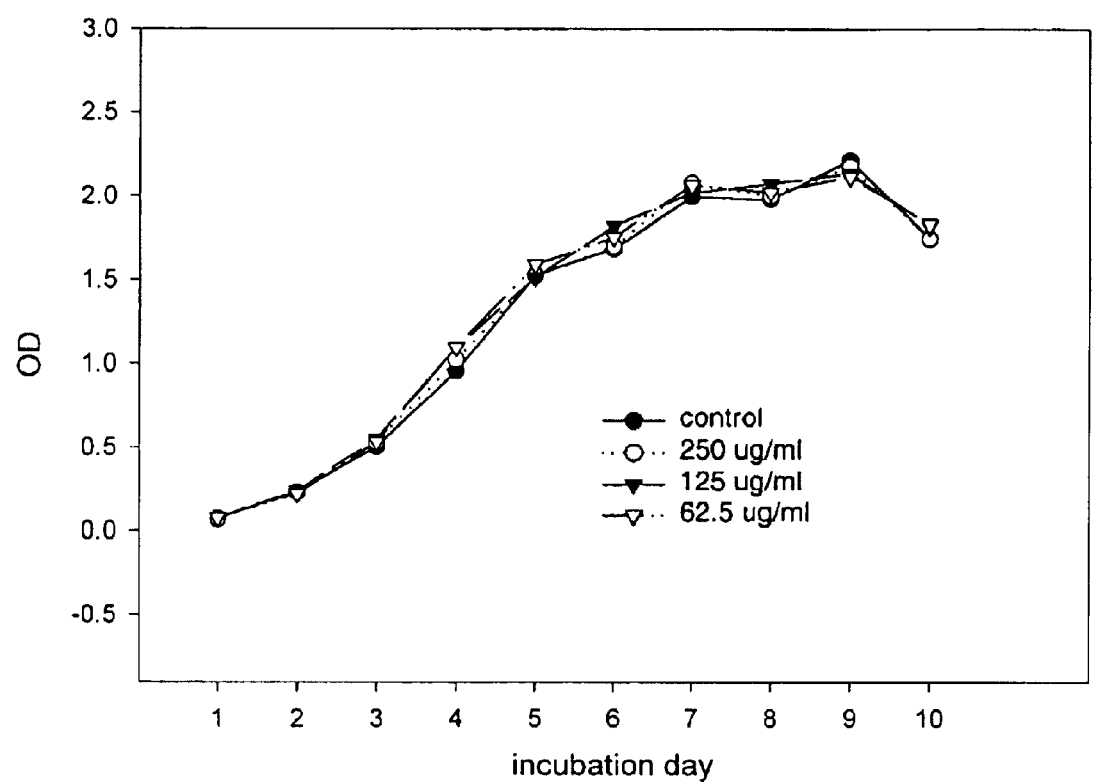
Figure 10:
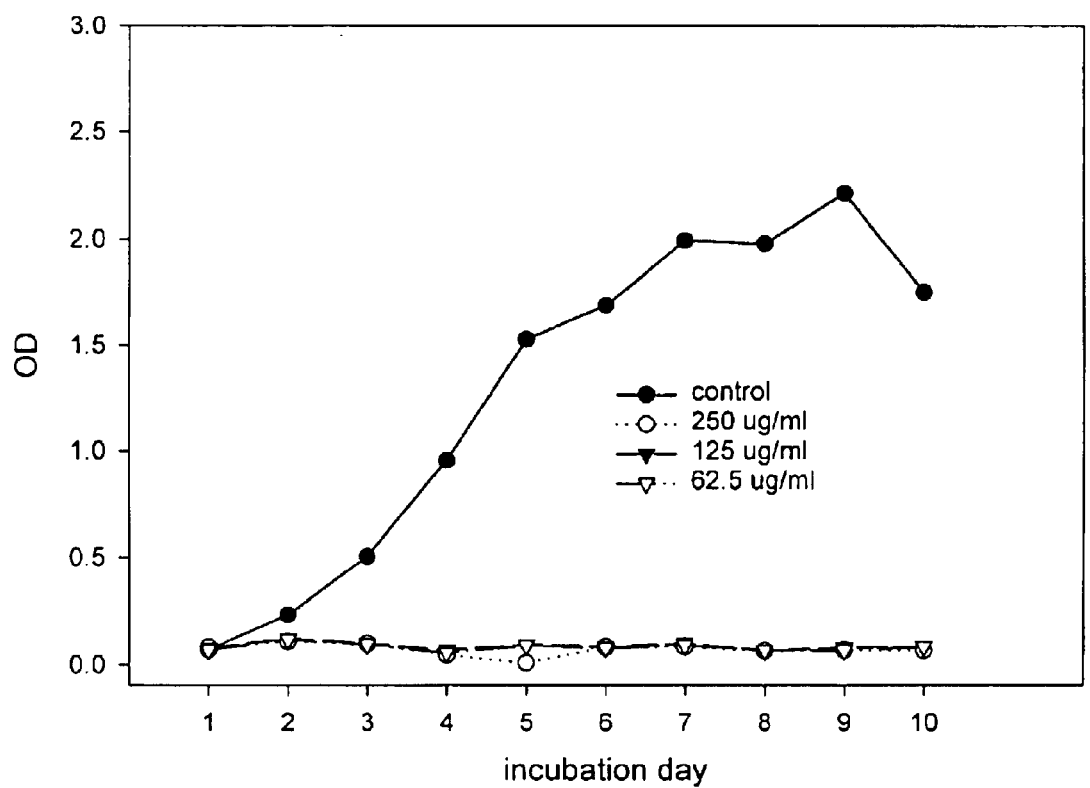
Figure 11:
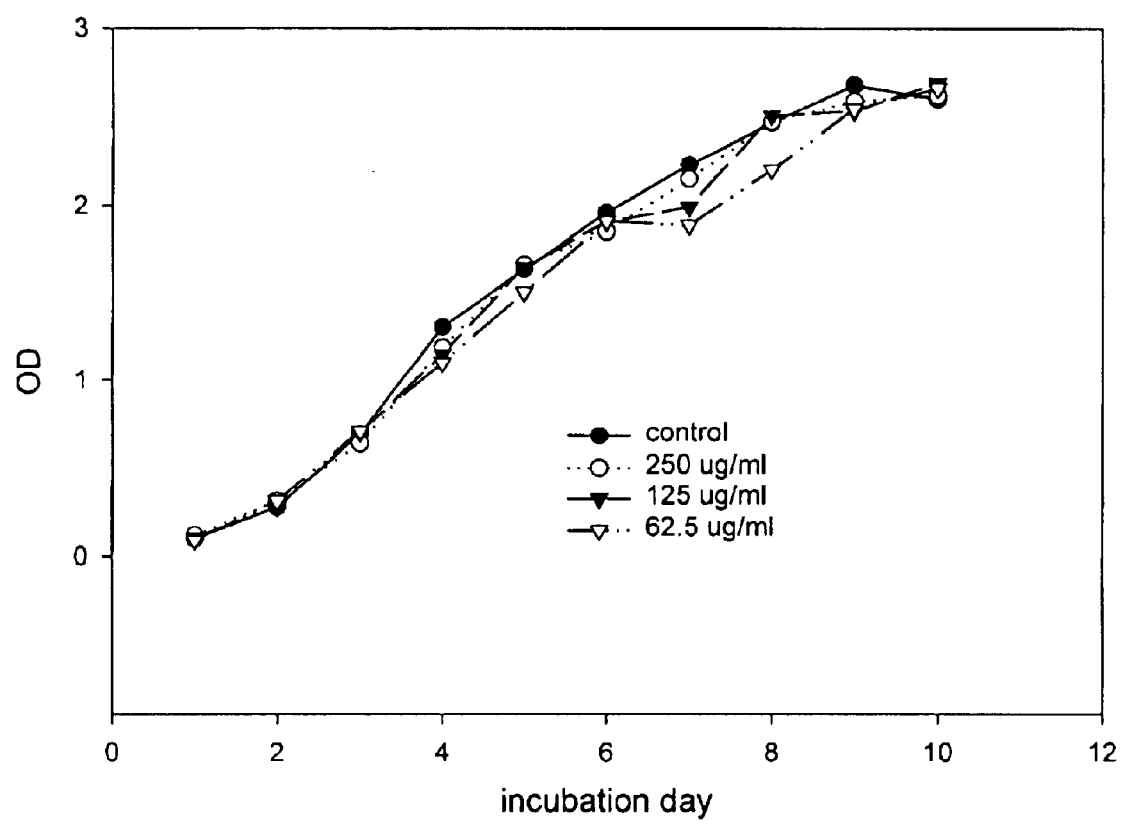
FIGS. 11–13 are graphs demonstrating the cytotoxicity against hTERT cells of a Transferrin-3-cholesterol conjugate, a Transferrin-rhodamine123 conjugate and a Transferrin-7-paclitaxel conjugate, respectively, at various concentrations under Protocol A.
Figure 12:
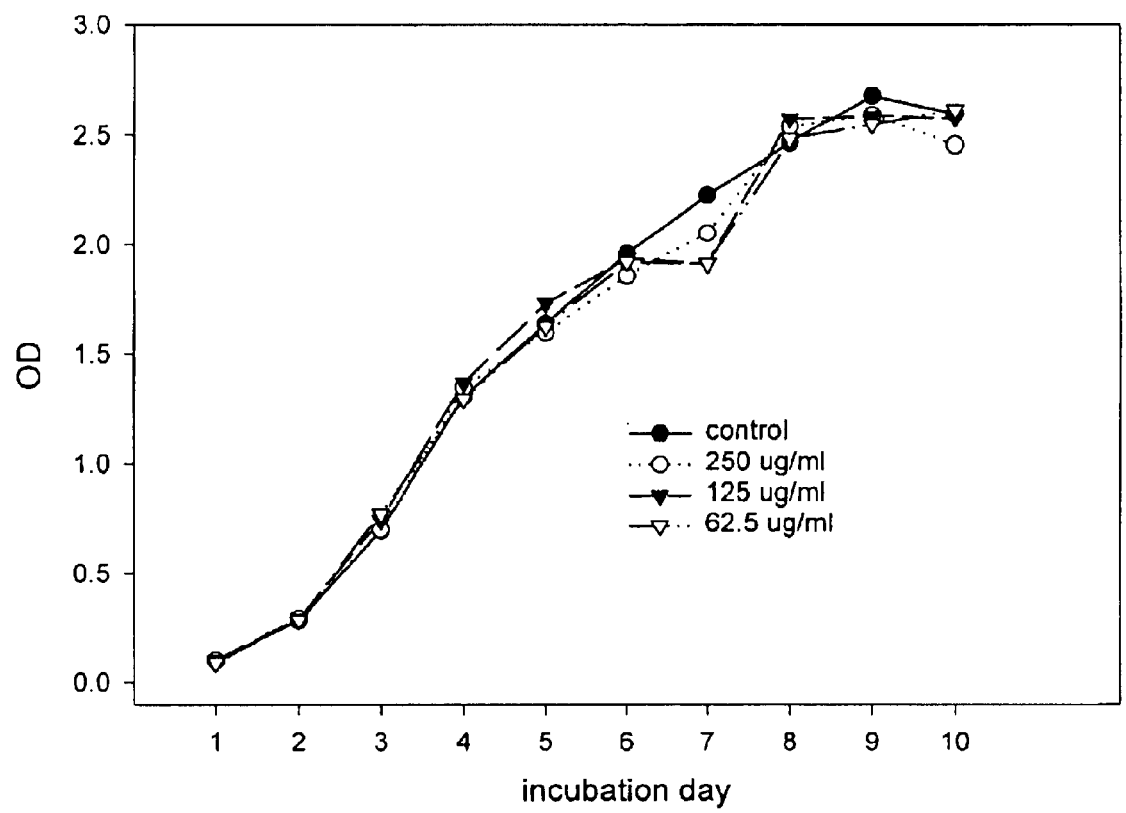
Figure 13:
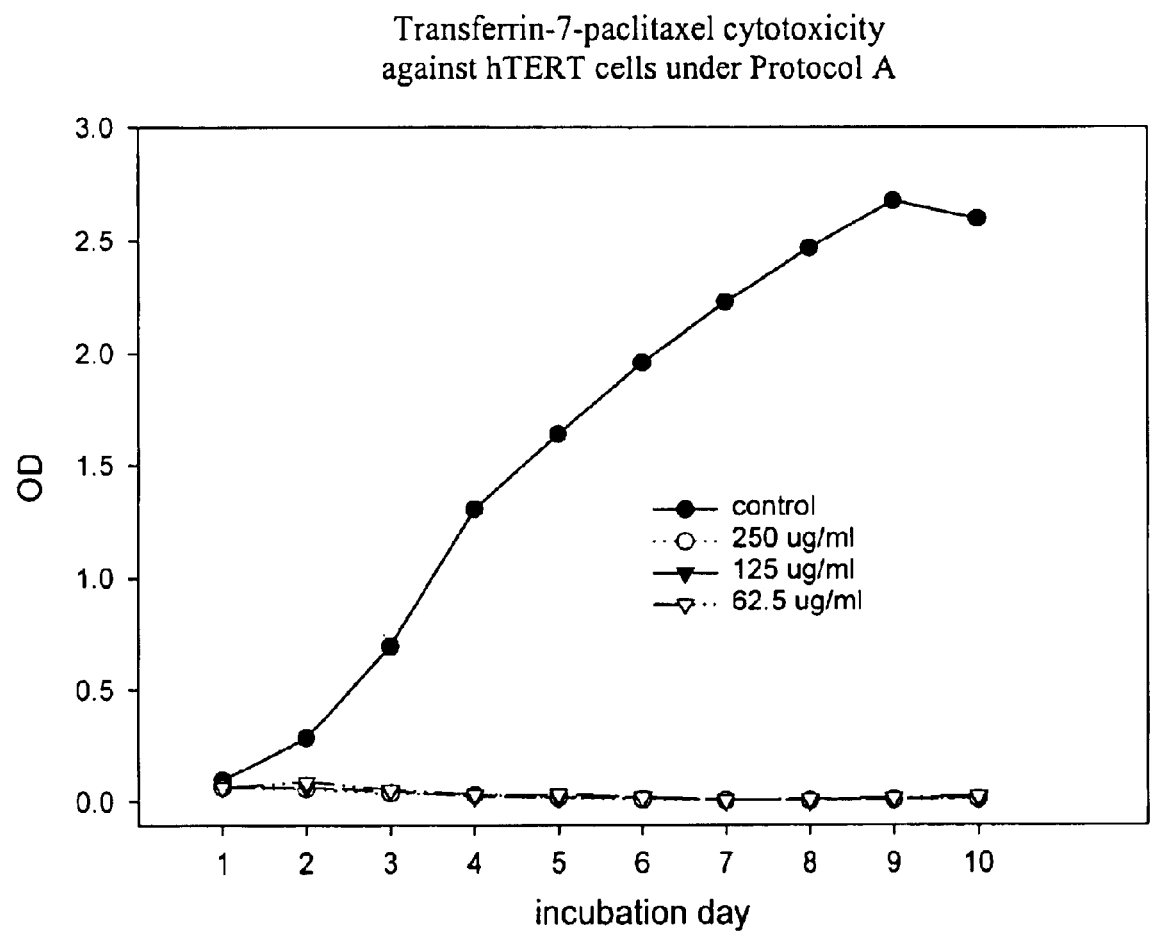

The first series of studies were conducted with the Transferrin-3-cholesterol conjugate, the Transferrin-rhodamine123 conjugate and the Transferrin-7-paclitaxel conjugate following Protocol A, in which various concentrations of test compounds ranging from 62.5–250 µg/ml were added on the day of plating, and media were replenished every 3 days, maintaining the same concentrations of the test compounds. As shown by plotting optical density versus time, the Transferrin-3-cholesterol conjugate and the Transferrin-rhodamine123 conjugate were not active with any of the cell lines (FIGS. 5, 6, 8, 9, 11, 12). On the other hand, complete inhibition of cell growth was observed with all of the concentrations of the Transferrin-7-paclitaxel conjugate that were tested (FIGS. 7, 10, 13).

Figure 14:
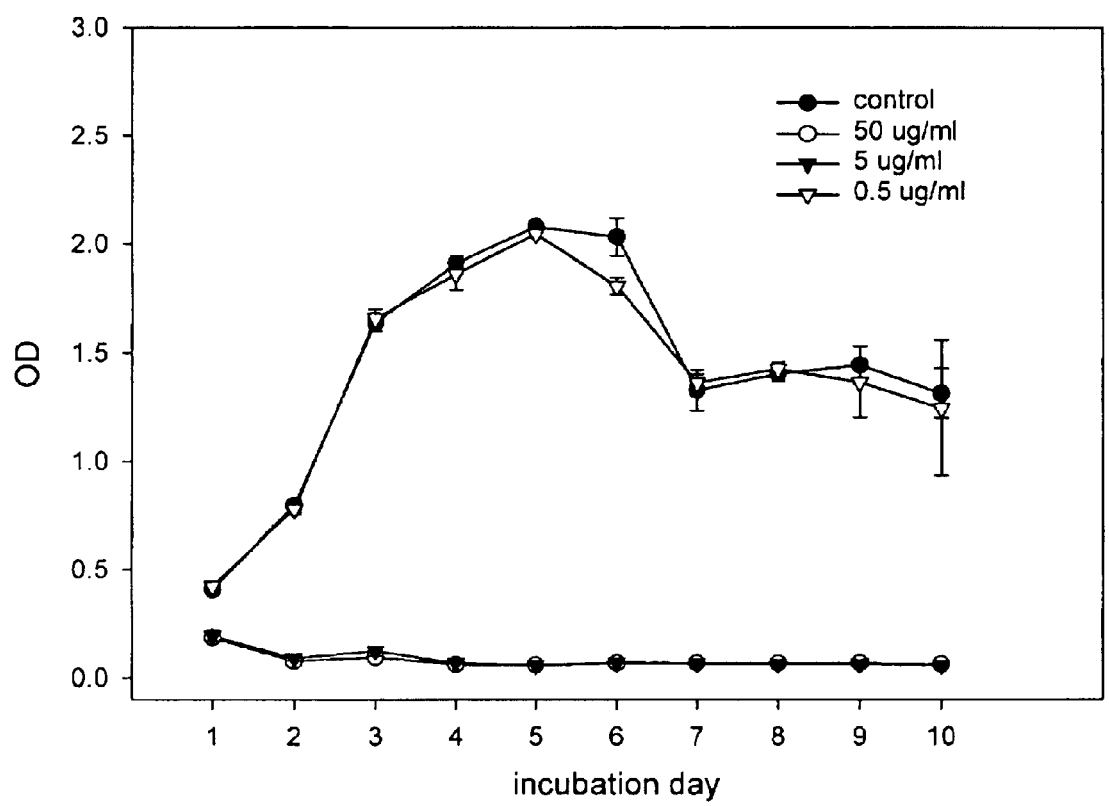
FIGS. 14–16 are graphs demonstrating the cytotoxicity against KB, Lu and hTERT cells, respectively, of a Transferrin-7-paclitaxel conjugate at various concentrations under Protocol A.
Figure 15:
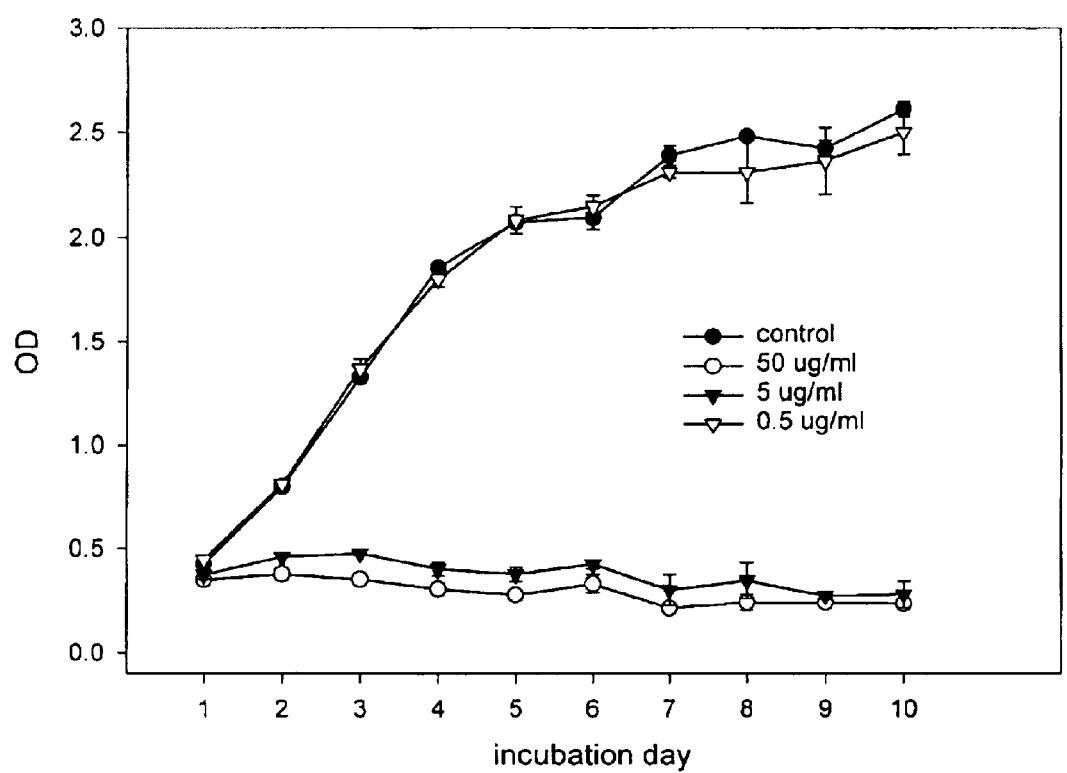
Figure 16:
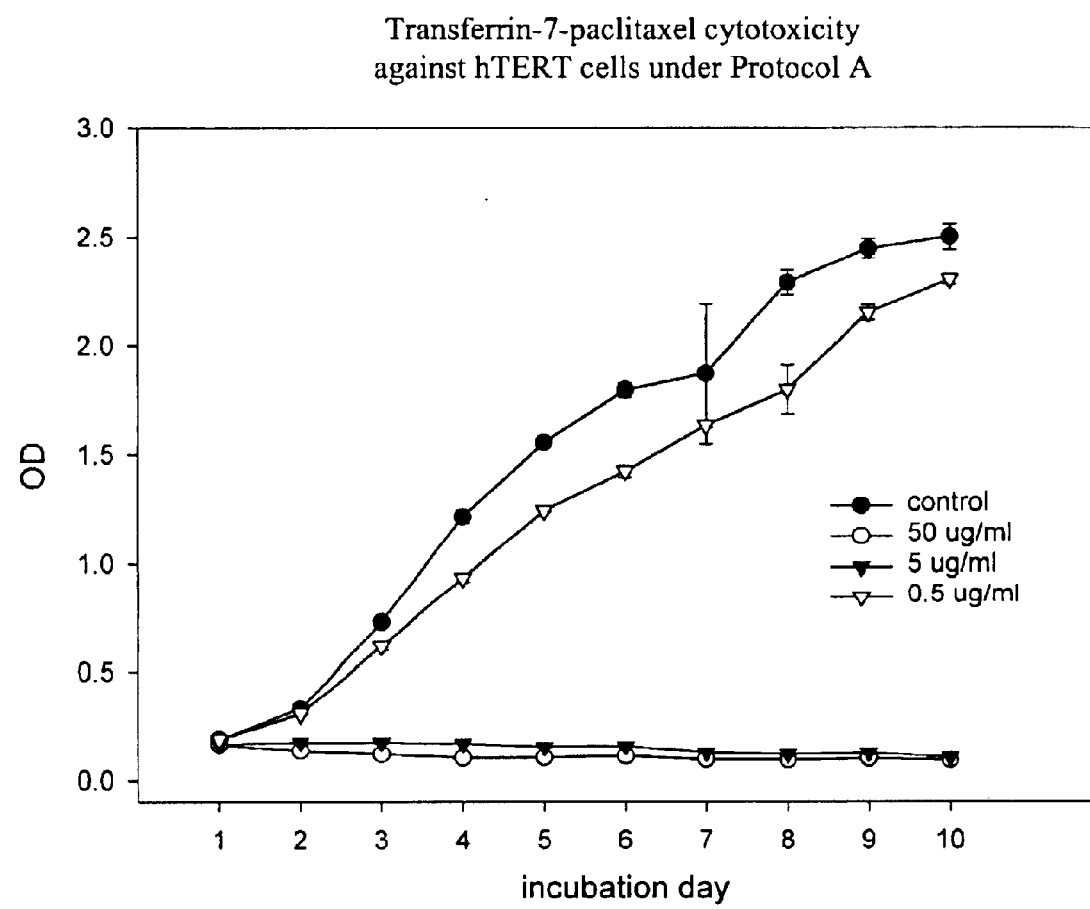

Therefore, the experiment was repeated with the Transferrin-7-paclitaxel conjugate with lower concentrations. As illustrated in FIG. 14, using Protocol A and KB cells, complete growth inhibition was observed with concentrations of 5 or 50 µg/ml, but no effect on growth was observed at a concentration of 0.5 µg/ml. Similar responses were observed with Lu and hTERT cells, as illustrated in FIGS. 15 and 16, respectively.

Figure 17:
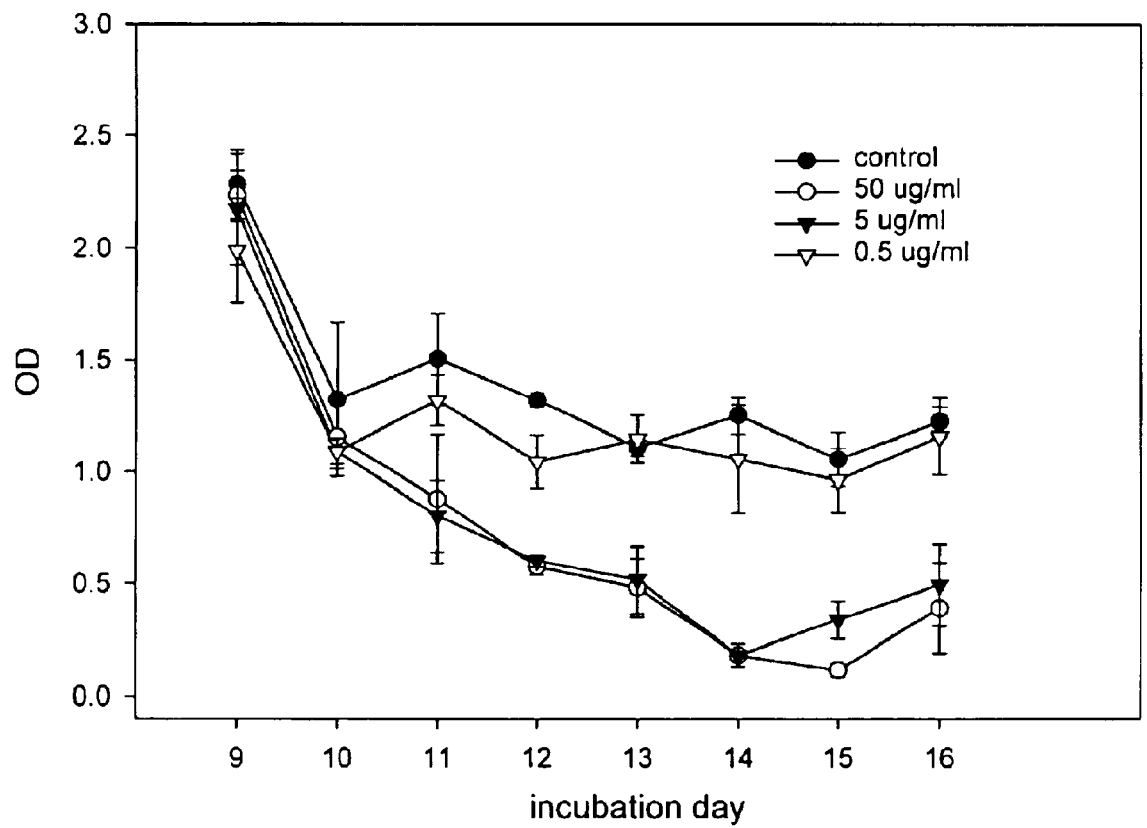
FIGS. 17–19 are graphs demonstrating the cytotoxicity against KB, Lu and hTERT cells, respectively, of a Transferrin-7-paclitaxel conjugate at various concentrations under Protocol B.

A similar profile was observed with KB cells following Protocol B, in which cells were grown until the $9^{th}$ day without changing the media, various concentrations of test compounds were added on the $9^{th}$ day, and compounds and media were then replenished every 3 days. At concentrations of 50 or 5 µg/ml, significant reduction in cell number was observed, but at 0.5 µg/ml, cell number paralleled that of the control (FIG. 17).

Figure 18:
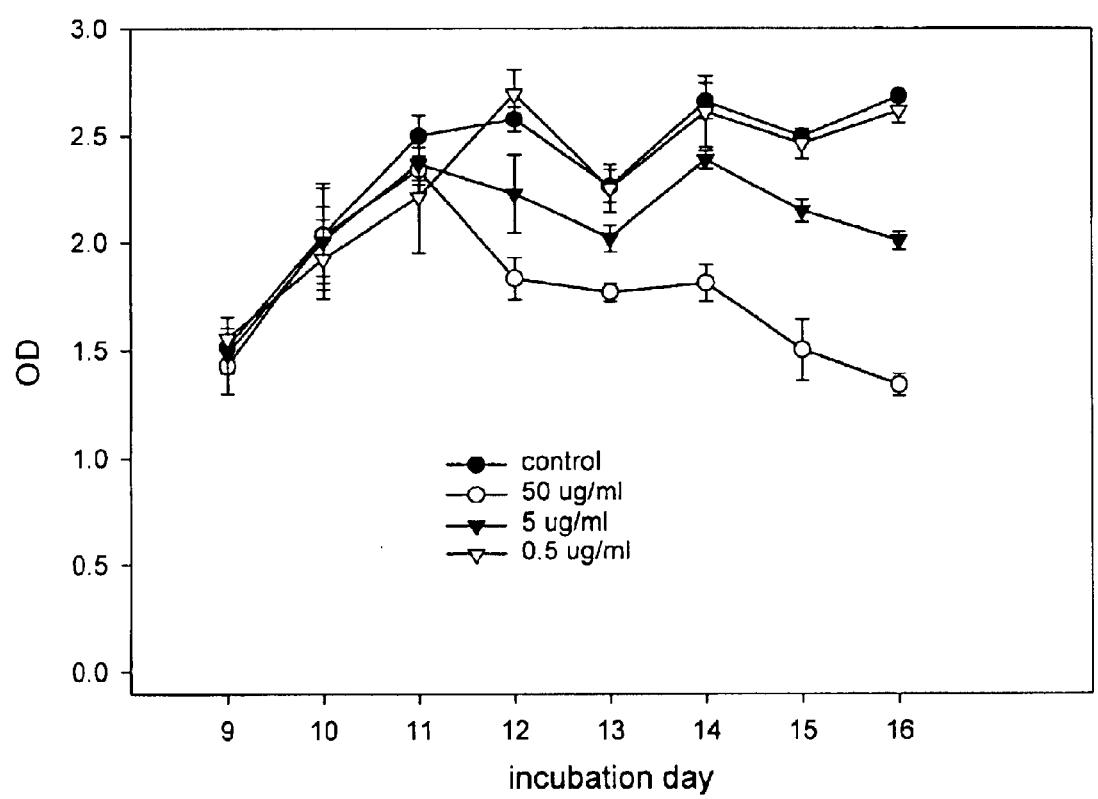

Lu cells were somewhat more resistant. At 50 µg/ml, a significant reduction in cell number was observed. This was diminished at a concentration of 5 µg/ml, and negated at a concentration of 0.5 µg/ml (FIG. 18).

Figure 19:
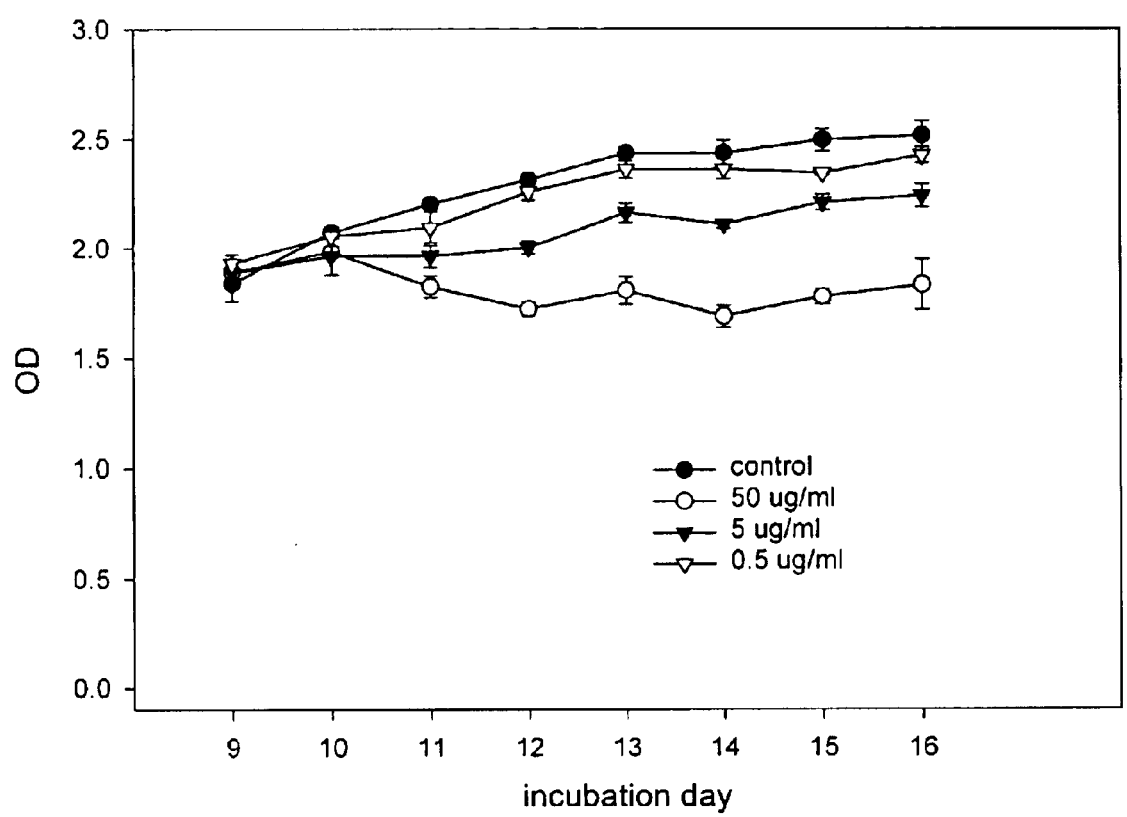

The weakest effect was observed with hTERT cells. Slight increases in cell growth were observed in the control cultures and cultures treated with 0.5 or 5 µg/ml of the Transferrin-7-paclitaxel conjugate. This growth was diminished when the cells were treated with 50 µg/ml, but on day 16, the cell number was still approximately the same as on day 9 (FIG. 19). These results suggest that the Transferrin-7-paclitaxel conjugate is primarily targeting cancer cells (KB and Lu) while not significantly affecting normal cells (hTERT), indicating that the Transferrin-7-paclitaxel conjugate and other protein-drug conjugates according to the present invention may provide a promising route to cancer treatment.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A molecular conjugate having the formula:

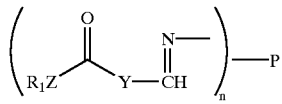

wherein:
(a) n is a conjugation number of said molecular conjugate;
(b) P is a de-amino moiety of a molecule having at least n accessible amino functionalities;
(c) $R_1$ is selected from:
  (1) a de-hydroxyl moiety of
    (i) a hydroxyl-bearing biologically active molecule and analogs and derivatives thereof of formula $R_1$—OH, and
  (2) a de-amino moiety of
    (i) an amino-bearing biologically active molecule and analogs and derivatives thereof of formula $R_1$—$NH_2$ or a salt or secondary amine thereof;
(d) where Z is —O— when $R_1$ is said de-hydroxyl moiety and Z is —NH— when $R_1$ is said de-amino moiety; and
(e) Y is selected from:
  (1) a straight or branched alkyl having 1 to 20 carbons optionally substituted with one or more phenyl,
  (2) a cycloalkyl optionally substituted with one or more alkyl or phenyl, and
  (3) an aromatic group optionally substituted with one or more alkyl, electron-withdrawing or electron-donating groups.

2. A molecular conjugate according to claim 1 wherein P is a protein.

3. A molecular conjugate according to claim 2 wherein said protein is Transferrin.

4. A molecular conjugate according to claim 1 wherein n is an integer from 1 to 5.

5. A molecular conjugate according to claim 1 wherein said biologically active molecule is a drug useful in cancer therapy.

6. A molecular conjugate according to claim 5 wherein said drug is a natural product cancer therapeutic drug.

7. A molecular conjugate according to claim 5 wherein said drug is selected from taxanes, camptothecins, epothilones, cucurbitacins, quassinoids, anthracyclines, and their analogs and derivatives.

8. A molecular conjugate according to claim 1 wherein $R_1$ is a moiety selected from 7-dehydroxyl paclitaxel, 10-dehydroxyl paclitaxel, 2'-dehydroxyl paclitaxel, 3'-debenzamido paclitaxel, 3-dehydroxyl cholesterol and 20-dehydroxyl camptothecin, and their analogs and derivatives.

9. A molecular conjugate according to claim 1 wherein Y is —$(CH_2)_r$— where r is an integer from 3 to 7.

10. A molecular conjugate according to claim 1 wherein $R_1$ is a 7-dehydroxyl paclitaxel moiety, Z is —O— and Y is —$(CH_2)_3$—.

11. A molecular conjugate according to claim 10 wherein P is Transferrin and n is 3.

12. A molecular conjugate according to claim 1 wherein $R_1$ is a 2'-dehydroxyl paclitaxel moiety, Z is —O— and Y is —$(CH_2)_4$—.

13. A molecular conjugate according to claim 12 wherein P is Transferrin and n is selected from 1 and 2.

14. A method of producing a molecular conjugate, comprising the steps of:

(A) reacting a first compound selected from:
  (1) a hydroxyl-bearing biologically active molecule and analogs and derivates thereof of formula $R_1$—OH, and
  (2) an amino-bearing biologically active molecule and analogs and derivatives thereof of formula $R_1$—$NH_2$ or a salt or secondary amine thereof, with a second compound selected from the formulas:

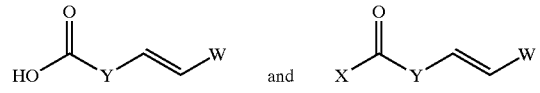

thereby to form a third compound of the formula:

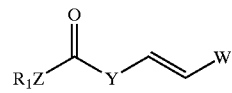

(B) converting said third compound to a fourth compound of the formula:

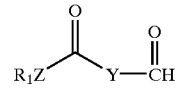

and (C) conjugating said fourth compound with a molecule having at least n accessible amino functionalities, thereby to form a molecular conjugate of the formula:

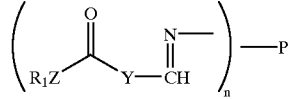

wherein:
(a) X is a halogen;
(b) Y is selected from:

(1) a straight or branched alkyl having 1 to 20 carbons optionally substituted with one or more phenyl,
(2) a cycloalkyl optionally substituted with one or more alkyl or phenyl, and
(3) an aromatic group optionally substituted with one or more alkyl or electron-withdrawing or electron-donating groups;

(c) W is selected from:
(1) H,
(2) a straight or branched alkyl having 1 to 20 carbons optionally substituted with one or more phenyl,
(3) a cycloalkyl optionally substituted with one or more alkyl or phenyl, and
(4) an aromatic group optionally substituted with one or more alkyl or electron-withdrawing or electron-donating groups;

(d) where $R_1$ is a de-hydroxyl moiety of said first compound and Z is —O— when said first compound is said hydroxyl-bearing biologically active molecule and analogs and derivatives thereof;

(e) where $R_1$ is a de-amino moiety of said first compound and Z is —NH— when said first compound is said amino-bearing biologically active molecule and analogs and derivatives thereof or a salt or secondary amine thereof;

(f) n is a conjugation number of said molecular conjugate; and (g) P is said molecule having at least n accessible amino functionalities.

15. A method according to claim 14 wherein W is H.
16. A method according to claim 14 wherein P is a protein.
17. A method according to claim 16 wherein said protein is Transferrin.
18. A method according to claim 14 wherein n is an integer from 1 to 5.
19. A method according to claim 14 wherein said biologically active molecule is a drug useful in cancer therapy.
20. A method according to claim 19 wherein said drug is a natural product cancer therapeutic drug.
21. A method according to claim 19 wherein said drug is selected from taxanes, camptothecins, epothilones, cucurbitacins, quassinoids, anthracyclines, and their analogs and derivatives.
22. A method according to claim 14 wherein $R_1$ is a moiety selected from 7-dehydroxyl paclitaxel, 10-dehydroxyl paclitaxel, 2'-dehydroxyl paclitaxel, 3'-debenzamido paclitaxel, 3-dehydroxyl cholesterol and 20-dehydroxyl camptothecin, and their analogs and derivatives.
23. A method according to claim 14 wherein Y is —(CH$_2$)$_r$— where r is an integer from 3 to 7.
24. A method according to claim 14 wherein the step of converting said third compound to said fourth compound includes oxidizing said third compound to a diol of the formula:

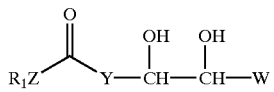

and thereafter oxidizing said diol to said fourth compound.
25. A method according to claim 14 wherein said molecule having at least n accessible amino functionalities is a Transferrin protein, and wherein the step of conjugating said fourth compound with said molecule includes mixing said fourth compound, DMSO and Transferrin in PBS-buffer to form a mixture containing the molecular conjugate.

26. A method according to claim 25 including the step of adding a quenching agent to said mixture containing the molecular conjugate.
27. A method according to claim 26 wherein said quenching agent is ethanolamine PBS solution.
28. A method according to claim 14 wherein $R_1$ is a 3-dehydroxyl cholesterol moiety and wherein the step of reacting said first compound with said second compound includes mixing cholesterol, methylene chloride, 5-hexeneoic acid, DCC and 4-PP under a nitrogen atmosphere.
29. A method according to claim 14 wherein $R_1$ is a 3-dehydroxyl cholesterol moiety and wherein the step of converting said third compound to said fourth compound includes mixing said third compound, THF, t-BuOH, water, NMO, NalO$_4$ and OsO$_4$ under a nitrogen atmosphere.
30. A method according to claim 14 wherein $R_1$ is a 20-dehydroxyl camptothecin moiety and wherein the step of reacting said first compound with said second compound includes mixing camptothecin, 5-hexeneoic acid, DMF, DIPC and 4-PP under a nitrogen atmosphere.
31. A method according to claim 14 wherein $R_1$ is a 20-dehydroxyl camptothecin moiety and wherein the step of converting said third compound to said fourth compound includes mixing said third compound, THF, acetone, ACN, water, t-BuOH, NMO, NalO$_4$ and OsO$_4$ under a nitrogen atmosphere.
32. A method of producing a Transferrin-7-paclitaxel conjugate for use in the treatment of cancer, comprising the steps of:

(A) protecting paclitaxel at the 2'-hydroxyl position to form a first compound of the formula

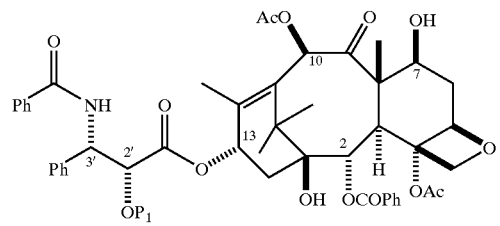

(B) reacting said first compound with a second compound selected from the formulas:

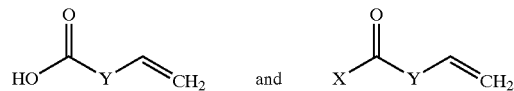

thereby to form a third compound of the formula:

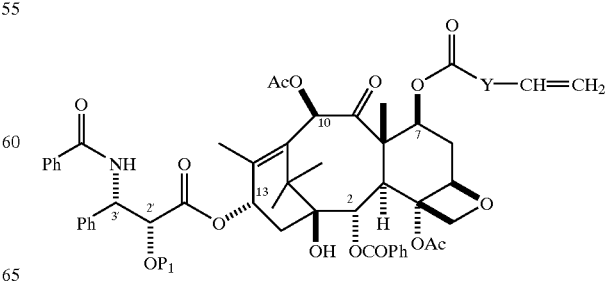

(C) converting said third compound to a fourth compound of the formula:

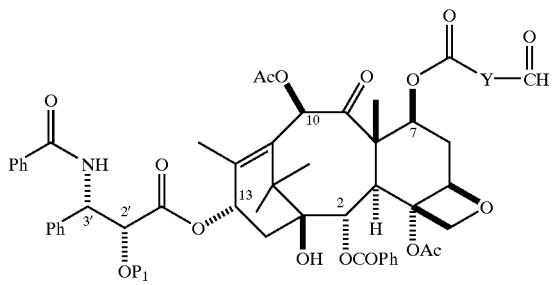

(D) deprotecting said fourth compound at the 2'-position to form a fifth compound of the formula:

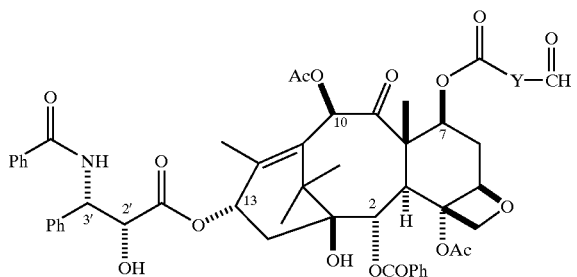

and (E) conjugating said fifth compound with Transferrin to form a molecular conjugate having the formula:

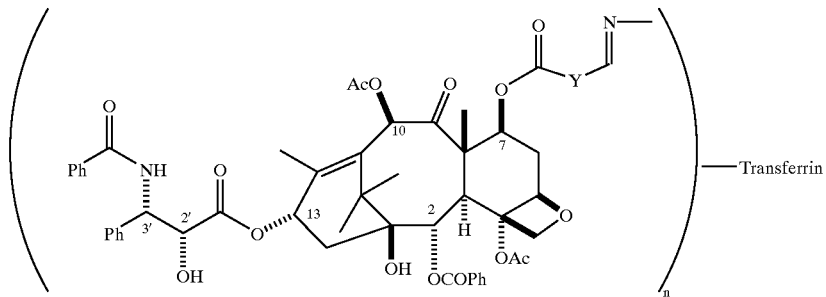

wherein:
(a) n is an integer from 1 to 5;
(b) $P_1$ is a hydroxyl protecting group;
(c) X is a halogen; and
(d) Y is selected from:
  (1) a straight or branched alkyl having 1 to 20 carbons optionally substituted with one or more phenyl,
  (2) a cycloalkyl optionally substituted with one or more alkyl or phenyl, and
  (3) an aromatic group optionally substituted with one or more alkyl, electron-withdrawing or electron-donating groups.

33. A method according to claim 32 wherein the step of reacting said first compound with said second compound includes mixing said first compound, methylene chloride, 5-hexenoic acid, DIPC and 4-PP under a nitrogen atmosphere.

34. A method according to claim 32 wherein the step of converting said third compound to said fourth compound includes mixing said third compound, ACN, THE, water, NMO, $NaIO_4$, $OsO_4$ and t-BuOH under a nitrogen atmosphere.

35. A method according to claim 32 wherein the step of deprotecting said fourth compound includes mixing said fourth compound, TBAF and THF under a nitrogen atmosphere.

36. A method according to claim 32 wherein the step of conjugating said fifth compound with Transferrin includes mixing said fifth compound, DMSO and Transferrin in PBS-Bufter/DMSO solution.

37. A method of producing a Transferrin-2'-paclitaxel conjugate for use in the treatment of cancer, comprising the steps of:

(A) reacting a first compound of the formula:

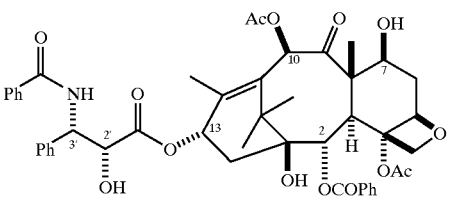

with a second compound selected from the formulas:

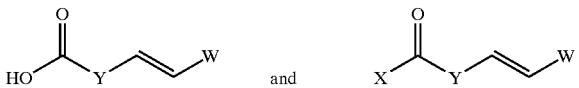

thereby to form a third compound of the formula:

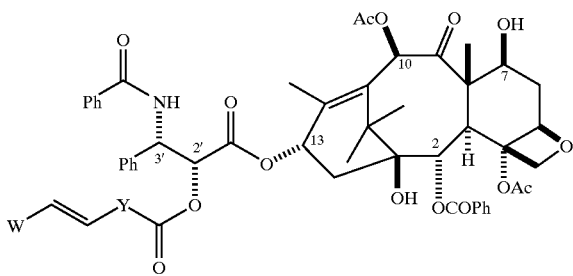

(B) converting said third compound to a fourth compound of the formula:

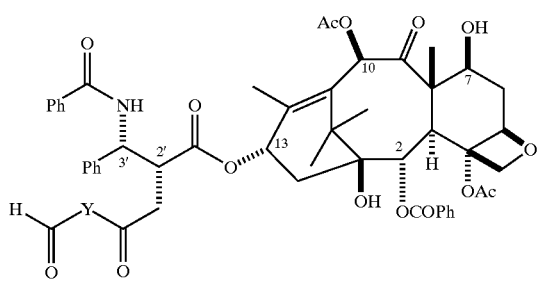

and (C) conjugating said fourth compound with Transferrin to form a molecular conjugate having the formula:

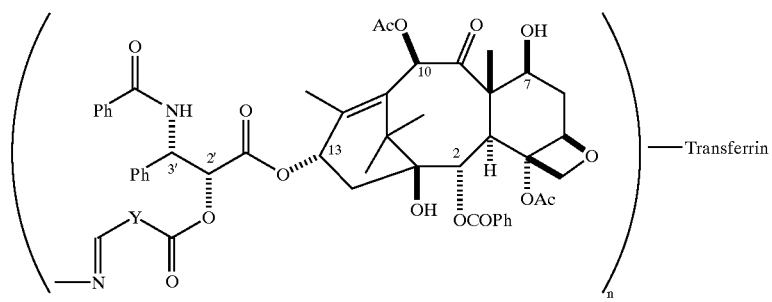

wherein:
(a) n is an integer from 1 to 5;
(b) X is a halogen;
(c) W is selected from:
  (1) H,
  (2) a straight or branched alkyl having 1 to 20 carbons optionally substituted with one or more phenyl,
  (3) a cycloalkyl optionally substituted with one or more alkyl or phenyl, and
  (4) an aromatic group optionally substituted with one or more alkyl or electron-withdrawing or electron-donating groups, and
(d) Y is selected from:
  (1) a straight or branched alkyl having 1 to 20 carbons optionally substituted with one or more phenyl,
  (2) a cycloalkyl optionally substituted with one or more alkyl or phenyl, and
  (3) an aromatic group optionally substituted with one or more alkyl, electron-withdrawing or electron-donating groups.

38. A method according to claim 37 wherein the step of reacting said first compound with said second compound includes mixing said first compound, methylene chloride, 5-heptenoic acid, DIPC and 4-PP under a nitrogen atmosphere.

39. A method according to claim 37 wherein the step of reacting said first compound with said second compound includes mixing said first compound, methylene chloride, oleic acid, DIPC and 4-PP under a nitrogen atmosphere.

40. A method according to claim 37 wherein the step of converting said third compound to said fourth compound includes mixing said third compound, acetone, water, NMO, NaIO$_4$, OsO$_4$ and t-BuOH under a nitrogen atmosphere.

41. A method according to claim 32 wherein the step of conjugating said fourth compound with Transferrin includes mixing said fourth compound, DMSO and Transferrin in PBS-Buffer/DMSO solution.

42. A method of producing a Transferrin-3'-paclitaxel conjugate for use in the treatment of cancer, comprising the steps of:

(A) reacting a first compound of the formula:

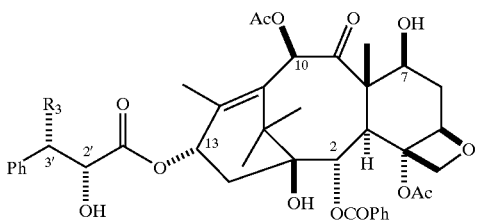

with a second compound selected from the formulas:

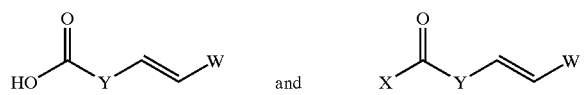

thereby to form a third compound of the formula:

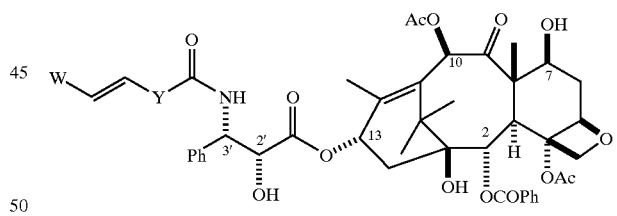

(B) converting said third compound to a fourth compound of the formula:

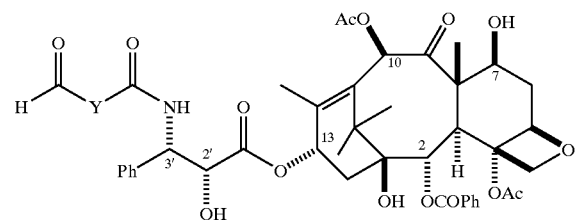

and (C) conjugating said fourth compound with Transferrin to form a molecular conjugate having the formula:

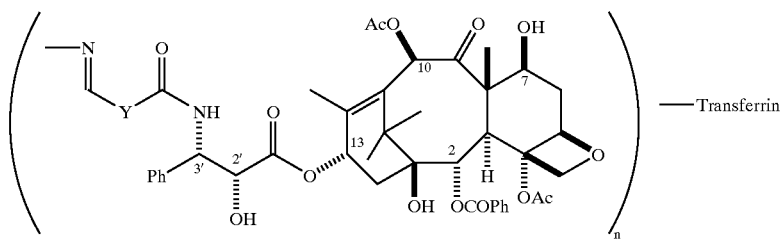

wherein
(a) n is an integer from 1 to 5;
(b) $R_3$ is selected from:
(1) $NH_2$, and
(2) $NH_2HA$ where HA is selected from:
(i) an organic acid and
(ii) a mineral acid;
(c) X is a halogen;
(d) W is selected from:
(1) H,
(2) a straight or branched alkyl having 1 to 20 carbons optionally substituted with one or more phenyl,
(3) a cycloalkyl optionally substituted with one or more alkyl or phenyl, and
(4) an aromatic group optionally substituted with one or more alkyl or electron-withdrawing or electron-donating groups; and
(e) Y is selected from:
(1) a straight or branched alkyl having 1 to 20 carbons optionally substituted with one or more phenyl,
(2) a cycloalkyl optionally substituted with one or more alkyl or phenyl, and
(3) an aromatic group optionally substituted with one or more alkyl, electron-withdrawing or electron-donating groups.

43. A method according to claim 42 wherein the step of reacting said first compound with said second compound includes mixing said first compound, methylene chloride, 5-heptenoic acid, DCC and 4-PP under a nitrogen atmosphere.

44. A method according to claim 42 wherein the step of reacting said first compound with said second compound includes first freeing said first compond to its corresponding amine.

45. A method according to claim 42 wherein the step of converting said third compound to said fourth compound includes mixing said third compound, ACN, water, NMO, $NaIO_4$, $OsO_4$ and THF under a nitrogen atmosphere.

46. A method according to claim 42 wherein the step of conjugating said fourth compound with Transferrin includes mixing said fourth compound, DMSO and Transferrin in PBS-Buffer/DMSO solution.

47. A method of producing a Transferrin-20-camptothecin conjugate for use in the treatment of cancer, comprising the steps of:

(A) reacting a first compound of the formula:

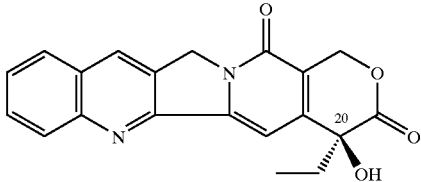

with a second compound selected from the formulas:

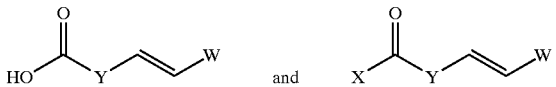

thereby to form a third compound of the formula:

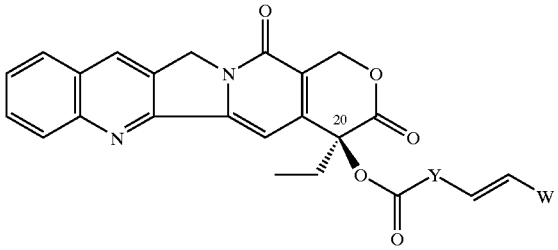

(B) converting said third compound to a fourth compound of the formula:

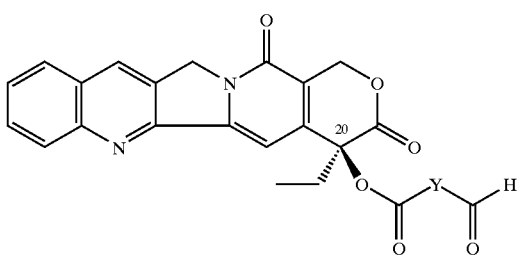

(C) conjugating said fourth compound with Transferrin to form a molecular conjugate having the formula:

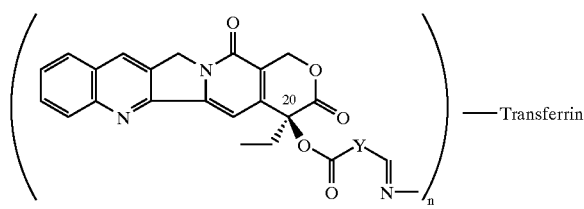

wherein:
(a) n is an integer from 1 to 5;
(b) X is a halogen;
(c) W is selected from:
(1) H,
(2) a straight or branched alkyl having 1 to 20 carbons optionally substituted with one or more phenyl,
(3) a cycloalkyl optionally substituted with one or more alkyl or phenyl, and
(4) an aromatic group optionally substituted with one or more alkyl or electron-withdrawing or electron-donating groups; and
(d) Y is selected from:
(1) a straight or branched alkyl having 1 to 20 carbons optionally substituted with one or more phenyl,
(2) a cycloalkyl optionally substituted with one or more alkyl or phenyl, and
(3) an aromatic group optionally substituted with one or more alkyl, electron-withdrawing or electron-donating groups.

48. A method according to claim 47 wherein the step of reacting said first compound with said second compound includes mixing said first compound, 5-hexenoic acid, DMF, DIPC and 4-PP under nitrogen atmosphere.

49. A method according to claim 47 wherein the step of converting said third compound to said fourth compound includes mixing said third compound, acetone, ACN, THF, water, NMO, NaIO$_4$, OsO$_4$ and t-BuOH under a nitrogen atmosphere.

50. A method according to claim 47 wherein the step of conjugating said fourth compound with Transferrin includes mixing said fourth compound, DMSO and Transferrin in PBS-Buffer/DMSO solution.

51. A compound useful in the formation of a Transferrin-Rhodamine 123 conjugate, said compound having the formula:

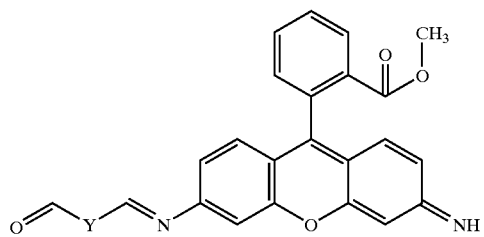

wherein Y is selected from:
(1) a straight or branched alkyl having 1 to 20 carbons optionally substituted with one or more phenyl,
(2) a cycloalkyl optionally substituted with one or more alkyl or phenyl, and
(3) an aromatic group optionally substituted with one or more alkyl, electron-withdrawing or electron-donating groups.

52. A compound according to claim 51 wherein Y is —(CH$_2$)$_3$—.

53. A method of producing a Transferrin-Rhodamine 123 conjugate, comprising:
adding an aldehyde of the formula:

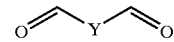

to a solution including Transferrin and including Rhodamine 123 of the formula:

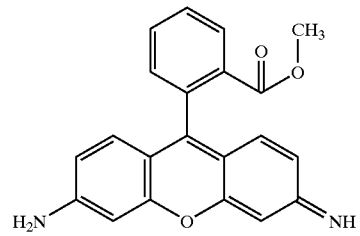

thereby to form a Transferrin-Rhodamine 123 conjugate of the formula:

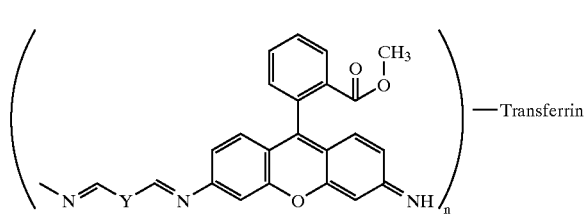

wherein:
(a) n is an integer from 1 to 5; and
(b) Y is selected from
(1) a straight or branched alkyl having 1 to 20 carbons optionally substituted with one or more phenyl,
(2) a cycloalkyl optionally substituted with one or more alkyl or phenyl, and
(3) an aromatic group optionally substituted with one or more alkyl, electron-withdrawing or electron-donating groups.

54. A method according to claim 53 wherein Transferrin, Hepes-buffer saline, rhodamine 123 and glutaraldehyde are mixed to form said Transferrin-Rhodamine 123 conjugate.

55. A method according to claim 54 including quenching said solution with a quenching agent.

56. A method according to claim 55 wherein said quenching agent is ethanolamine HBS solution.

57. A method of concentrating a biologically active molecule in selected target cells of a patient, comprising:
administering to the patient a selected dose of a molecular conjugate having the formula:

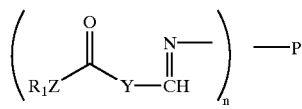

wherein:
(a) n is a conjugation number of said molecular conjugate;
(b) P is a de-amino moiety of a molecule having at least n accessible amino functionalities and which targets said selected cells,
(c) R$_1$ is selected from:

(1) a de-hydroxyl moiety of
   (i) a hydroxyl-bearing biologically active molecule and analogs and derivatives thereof of formula $R_1$—OH, and
(2) a de-amino moiety of
   (i) an amino-bearing biologically active molecule and analogs and derivatives thereof of formula $R_1$—$NH_2$ or a salt or secondary amine thereof;
(d) where Z is —O— when $R_1$ is selected from said de-hydroxyl moiety and Z is —NH— when $R_1$ is selected from said de-amino moiety; and
(e) Y is selected from:
   (1) a straight or branched alkyl having 1 to 20 carbons optionally substituted with one or more phenyl,
   (2) a cycloalkyl optionally substituted with one or more alkyl or phenyl, and
   (3) an aromatic group optionally substituted with one or more alkyl, electron-withdrawing or electron-donating groups.

58. A method according to claim 57 wherein P is a protein.
59. A method according to claim 58 wherein said protein is Transferrin.
60. A method according to claim 57 wherein n is an integer from 1 to 5.
61. A method according to claim 57 wherein said biologically active molecule is a drug useful in cancer therapy.
62. A method according to claim 61 wherein said drug is a natural product cancer therapeutic drug.
63. A method according to claim 61 wherein said drug is selected from taxanes, camptothecins, epothilones, cucurbitacins, quassinoids, anthracyclines, and their analogs and derivatives.
64. A method according to claim 57 wherein $R_1$ is a moiety selected from 7-dehydroxyl paclitaxel, 10-dehydroxyl paclitaxel, 2'-dehydroxyl paclitaxel, 3'-debenzamido paclitaxel, 3-dehydroxyl cholesterol and 20-dehydroxyl camptothecin, and their analogs and derivatives.
65. A method according to claim 57 wherein Y is —$(CH_2)_r$— where r is an integer from 3 to 7.
66. A compound useful in the formation of a molecular conjugate, said compound having the formula:

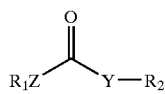

wherein
(a) $R_1$ is a 7-dehydroxyl paclitaxel moiety;
(b) Z is —O—;
(c) $R_2$ is selected from —CH=CH(W), —CH(OH)CH(OH)W, and —C(O)H;
(d) W is selected from:
   (1) H,
   (2) a straight or branched alkyl having 1 to 20 carbons optionally substituted with one or more phenyl,
   (3) a cycloalkyl optionally substituted with one or more alkyl or phenyl, and
   (4) an aromatic group optionally substituted with one or more alkyl or electron-withdrawing or electron-donating groups; and
(e) Y is —$(CH_2)_3$—.

67. A compound useful in the formation of a molecular conjugate, said compound having the formula:

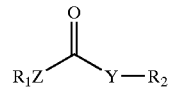

wherein
(a) $R_1$ is a 7-dehydroxyl 2'-protected paclitaxel moiety;
(b) Z is —O—;
(c) $R_2$ is selected from —CH=$CH_2$ and —CH(OH)$CH_2$(OH); and
(d) Y is selected from:
   (1) a straight or branched alkyl having 1 to 20 carbons optionally substituted with one or more phenyl,
   (2) a cycloalkyl optionally substituted with one or more alkyl or phenyl, and
   (3) an aromatic group optionally substituted with one or more alkyl or electron-withdrawing or electron-donating groups.

68. A compound useful in the formation of a molecular conjugate, said compound having the formula:

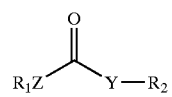

wherein
(a) $R_1$ is a 7-dehydroxyl-2'-hydroxyl paclitaxel moiety;
(b) Z is —O—;
(c) $R_2$ is —C(O)H; and
(d) Y is selected from:
   (1) a straight or branched alkyl having 1 to 20 carbons optionally substituted with one or more phenyl,
   (2) a cycloalkyl optionally substituted with one or more alkyl or phenyl, and
   (3) an aromatic group optionally substituted with one or more alkyl or electron-withdrawing or electron-donating groups.

* * * * *